United States Patent
Binch et al.

(10) Patent No.: US 8,642,779 B2
(45) Date of Patent: Feb. 4, 2014

(54) COMPOSITIONS USEFUL AS INHIBITORS OF PROTEIN KINASES

(75) Inventors: Hayley Binch, Encinitas, CA (US);
Simon Everitt, Oxfordshire (GB);
Francesca Mazzei, Wallingford (GB);
Daniel Robinson, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 15 days.

(21) Appl. No.: 12/634,136

(22) Filed: Dec. 9, 2009

(65) Prior Publication Data

US 2010/0087467 A1    Apr. 8, 2010

Related U.S. Application Data

(62) Division of application No. 10/949,714, filed on Sep. 23, 2004, now Pat. No. 7,652,135.

(60) Provisional application No. 60/505,236, filed on Sep. 23, 2003.

(51) Int. Cl.
*C07D 231/54* (2006.01)
*C07D 401/00* (2006.01)
*C07D 409/00* (2006.01)

(52) U.S. Cl.
USPC .................... 548/360.5; 544/300; 549/59

(58) Field of Classification Search
USPC ........ 544/297, 300; 548/356.5, 360.5; 549/59
See application file for complete search history.

(56) References Cited

U.S. PATENT DOCUMENTS

| | | | |
|---|---|---|---|
| 5,508,300 | A | 4/1996 | Duplantier |
| 5,596,013 | A | 1/1997 | Duplantier |
| 5,783,576 | A | 7/1998 | Roos et al. |
| 5,843,912 | A | 12/1998 | Hosmane et al. |
| 6,187,774 | B1 | 2/2001 | Tanaka et al. |
| 7,041,687 | B2 | 5/2006 | Binch et al. |
| 7,141,568 | B2 * | 11/2006 | Fancelli et al. ............ 514/234.2 |
| 2002/0103229 | A1 | 8/2002 | Bhagwat et al. |
| 2003/0171357 | A1 | 9/2003 | Fancelli et al. |
| 2004/0009968 | A1 | 1/2004 | Binch et al. |
| 2004/0077564 | A1 | 4/2004 | Hosmane et al. |
| 2007/0037790 | A1 * | 2/2007 | Abrate et al. ................ 514/215 |

FOREIGN PATENT DOCUMENTS

| | | | |
|---|---|---|---|
| EP | 9986422 | A2 | 8/1983 |
| EP | 0086422 | B1 | 9/1987 |
| EP | 15150516 | | 5/2003 |
| EP | 726899 | | 5/2009 |
| WO | 9512584 | | 5/1995 |
| WO | 9512592 | | 5/1995 |
| WO | 9519362 | | 7/1995 |
| WO | 0039131 | | 7/2000 |
| WO | 0071508 | A2 | 11/2000 |
| WO | 0076971 | A2 | 12/2000 |
| WO | 0156988 | A1 | 8/2001 |
| WO | 0185719 | A1 | 11/2001 |
| WO | 0210137 | A2 | 2/2002 |
| WO | 0212242 | | 2/2002 |
| WO | WO 0212242 | * | 2/2002 ........... C07D 487/04 |
| WO | 02083648 | A1 | 10/2002 |
| WO | 02100833 | A1 | 12/2002 |
| WO | 03101968 | | 12/2003 |
| WO | 2004013144 | | 2/2004 |
| WO | 2004014374 | | 2/2004 |
| WO | 2004-056827 | | 7/2004 |
| WO | WO 2004080457 | * | 9/2004 ......... A61K 31/4162 |

OTHER PUBLICATIONS

Nicolaides E.D. et al., "Potential antiviral agents", Journal of Medicinal Chemistry, 11(1):74-79, (1968).
Ostrowska K. et al., "Sulfuration reactions of pyrrolidine derivatives with Lawesson's reagent", Journal of Chemical Research, 5:236-237, (1996).

* cited by examiner

*Primary Examiner* — Nizal Chandrakumar
(74) *Attorney, Agent, or Firm* — Rory C. Stewart

(57) ABSTRACT

The present invention provides compounds of formula I:

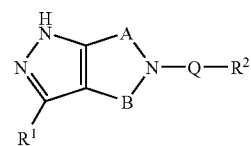

or a pharmaceutically acceptable derivative thereof, wherein A, B, Q, $R^1$, and $R^2$ are as described in the specification. These compounds are inhibitors of protein kinase, particularly inhibitors of AKT or PDK1 kinase, mammalian protein kinases involved in proliferative and neurodegenerative disorders. The invention also provides pharmaceutical compositions comprising the compounds of the invention, processes for preparing the compounds, and methods of utilizing those compositions in the treatment of various disorders.

4 Claims, No Drawings

COMPOSITIONS USEFUL AS INHIBITORS OF PROTEIN KINASES

CROSS-REFERENCE TO RELATED APPLICATIONS

This application is a divisional of U.S. patent application Ser. No. 10/949,714, filed Sep. 23, 2004; which claims the benefit of U.S. Provisional Patent Application No. 60/505,236 filed Sep. 23, 2003, the contents of which are incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor α (TNF-α)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents. A challenge has been to find protein kinase inhibitors that act in a selective manner. Since there are numerable protein kinases that are involved in a variety of cellular responses, non-selective inhibitors may lead to unwanted side effects.

AKT (also known as PKB or Rac-PK beta), a serine/threonine protein kinase, has been shown to be overexpressed in several types of cancer and is a mediator of normal cell functions [(Khwaja, A., *Nature*, 401, pp. 33-34, 1999); (Yuan, Z. Q., et al., *Oncogene*, 19, pp. 2324-2330, 2000); (Namikawa, K., et al., *J Neurosci.*, 20, pp. 2875-2886, 2000)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., *Proc. Natl. Acad. Sci. USA*, 89, pp. 9267-9271, 1992); (Brodbeck, D. et al., *J. Biol. Chem.* 274, pp. 9133-9136, 1999)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., *Mol. Cell. Biol.*, 17, pp. 1595-1606, 1997); (Hemmings, B. A., *Science*, 275, pp. 628-630, 1997)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., *J. Biol. Chem.*, 273, pp. 7201-7204, 1998), induction of differentiation and/or proliferation, protein synthesisans stress responses (Alessi, D. R. et al., *Curr. Opin. Genet. Dev.*, 8, pp. 55-62, 1998).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., *Proc. Natl. Acad. Sci. U.S.A.*, 89, pp. 9267-9271, 1992). It has also been found to be overexpressed in 12% of pancreatic cancers (Cheng, J. Q. et al., *Proc. Natl. Acad. Sci. U.S.A.*, 93, pp. 3636-3641, 1996). It was demonstrated that AKT-2 was overexpressed in 12% of ovarian carcinomas and that amplification of AKT was especially frequent in 50% of undifferentiated tumours, showing that AKT is also associated with tumour aggressiveness (Bellacosa, et al., *Int. J. Cancer*, 64, pp. 280-285, 1995).

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans*, 29, pp. 1, 2001). These include isoforms of protein kinase B (PKB, also known as AKT), p70 ribosomal S6 kinase (S6K) (Avruch, J. et al., *prog. Mol. Subcell. Biol.*, 2001, 26, pp. 115, 2001), and p90 ribosomal S6 kinase (Frödin, M. et al., *EMBO J.*, 19, pp. 2924-2934, 2000). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.*, 114, pp. 2903-2910, 2001), (Lawlor, M. A. et al., *EMBO J.*, 21, pp. 3728-3738, 2002)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.*, 9, pp. R93-R96, 1999). Many human cancers including prostate and NSCL have elevated PDK1 signaling pathway function resulting from a number of distinct genetic events such as PTEN mutations or over-expression of certain key regulatory proteins [(Graff, J. R., *Expert Opin. Ther. Targets*, 6, pp. 103-113, 2002), (Brognard, J., et al., *Cancer Res.*, 61, pp. 3986-3997, 2001)] Inhibition of PDK1 as a mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.*, 10, pp. 1439-1442, 2000). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell*, 100, pp. 57-70, 2000). PDK1 is a critical mediator of the PI3K signalling pathway, which regulates a multitude of cellular function including growth, proliferation and survival. Consequently inhibition of this pathway could affect four or more of the six defining requirements for cancer progression, as such it is anticipated that a PDK1 inhibitor will have an effect on the growth of a very wide range of human cancers.

Specifically, increased levels of PI3K pathway activity has been directly associated with the development of a number of human caners, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., *Cancer Res.*, 57, pp. 5221-5225, 1997), (Brognard, J. et al., *Cancer Res.*, 61, pp. 3986-3997, 2001), (Cheng, J. Q. et al., *Proc. Natl. Acad. Sci.*, 93, pp. 3636-3641, 1996), *Int. J. Cancer*, 64, pp. 280, 1995), (Graff, J. R., *Expert Opin. Ther. Targets*, 6, pp. 103-113, 2002), *Am. J. Pathol.*, 159, pp. 431, 2001)].

Additionally, decreased pathway function through gene knockout, gene knockdown, dominant negative studies and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.*, 93, pp. 3636-3641, 1996), *Neoplasia*, 3, pp. 278, 2001)], lung [(Brognard, J. et al., *Cancer Res.*, 61, pp. 3986-3997, 2001), *Neoplasia*, 3, pp. 278, 2001)], ovarian [(Hayakawa, J. et al., *Cancer Res.*, 60, pp. 5988-5994, 2000), *Neoplasia*, 3, pp. 278, 2001)], breast (*Mol. Cancer Ther.*, 1, pp. 707, 2002), colon [(*Neoplasia*, 3, pp. 278, 2001), (Arico, S. et al., *J. Biol. Chem.*, 277, pp. 27613-27621, 2002)], cervical (*Neoplasia*, 3, pp. 278, 2001), prostate [(*Endocrinology*, 142, pp. 4795, 2001), (Thakkar, H. et al. *J. Biol. Chem.*, 276, pp. 38361-38369, 2001), (Chen, X. et al., *Oncogene*, 20, pp. 6073-6083, 2001)] and brain (glioblastomas) [(Flynn, P. et al., *Curr. Biol.*, 10, pp. 1439-1442, 2000)].

Accordingly, there is a great need to develop inhibitors of AKT and PDK1 protein kinases that are useful in treating various diseases or conditions associated with AKT and PDK1 activation, particularly given the inadequate treatments currently available for the majority of these disorders.

SUMMARY OF THE INVENTION

This invention provides compounds having the formula I:

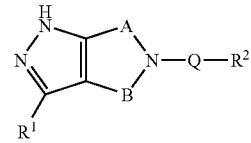

or a pharmaceutically acceptable salt thereof, wherein A, B, Q, $R^1$, and $R^2$ are as defined below.

These compounds, and pharmaceutically acceptable compositions thereof, are useful for treating or lessening the severity of a variety of disorders, including proliferative disorders and neurological disorders.

DESCRIPTION OF THE INVENTION

The present invention relates to a compound of formula I:

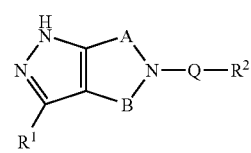

or a pharmaceutically acceptable salt thereof, wherein:
A is —$CH_2$— or —$CH_2C(R^a)(R^b)$—, wherein:
  $R^a$ and $R^b$ are independently hydrogen, an optionally substituted $C_{1-6}$ aliphatic group, or halogen, or $R^a$ and $R^b$ are taken together to form a 3-6 membered saturated or partially unsaturated ring having 0-2 heteroatoms independently selected from nitrogen, oxygen or sulfur;
B is A is —$CH_2$— or —$CH_2C(R^c)(R^d)$—, wherein:
  $R^c$ and $R^d$ are independently hydrogen, $C_{1-4}$ aliphatic, or halogen, or $R^c$ and $R^d$ are taken together to form a cyclopropyl ring;
$R^1$ is T-Ar;
each T is independently selected from a valence bond or a $C_{1-6}$ wherein up to two methylene units of T are optionally, and independently, replaced by —O—, —N(R)—, —S—, —N(R)C(O)—, —C(O)N(R)—, —C(O)—, or —$SO_2$—;
each R is independently selected from hydrogen or an optionally substituted $C_{1-6}$ aliphatic group, or:
  two R groups on the same nitrogen, taken together with the nitrogen atom attached thereto, form a 5-7 membered saturated, partially unsaturated, or aromatic ring having 1-3 heteroatoms independently selected from nitrogen, oxygen, or sulfur;
Q is a valence bond or a $C_{1-6}$ alkylidene chain, wherein up to two methylene units of Q are optionally, and independently, replaced by —O—, —N(R)—, —S—, —N(R)C(O)—, —C(O)N(R)—, —C(O)—, or —$SO_2$—;
$R^2$ is selected from Ar, $R^3$, or $C(R)(Ar)R^3$, wherein:
  R and $R^3$ optionally form a 5-7 membered saturated or partially unsaturated ring having 0-4 heteroatoms independently selected from nitrogen, oxygen, or sulfur;
each Ar is independently an optionally substituted ring selected from a 5-7 membered saturated, partially unsaturated, or fully unsaturated monocyclic ring having 0-4 heteroatoms independently selected from nitrogen, oxygen, or sulfur, or an 8-10 membered saturated, partially unsaturated, or fully unsaturated bicyclic ring having 0-4 heteroatoms independently selected from nitrogen, oxygen, or sulfur;

each $R^3$ is independently selected from R', $Ar^1$, W—$OR^5$, W—$OC(O)R^5$, W—$CONHR^5$, W—$OC(O)NHR^5$, W—$SR^5$, W—$N(R^4)_2$, N(R)(W—Ar), N(R)C(O)W—N$(R^4)_2$, or N(R)W—$N(R^4)_2$, wherein:

each W is independently a valence bond or a $C_{1-6}$ alkylidene chain;

R' is an optionally substituted $C_{1-6}$ aliphatic group;

each $Ar^1$ is independently selected from an optionally substituted 5-7 membered saturated, partially unsaturated, or fully unsaturated monocyclic ring having 0-4 heteroatoms independently selected from nitrogen, oxygen, or sulfur;

each $R^4$ is independently selected from R, $COR^5$, $CO_2R^5$, $CON(R^5)_2$, $SO_2R^5$, $SO_2N(R^5)_2$, or $Ar^1$; and each $R^5$ is independently selected from R or Ar;

provided that:

when one of A or B is —$CH_2$— and the other of A or B is —$CH_2CH_2$—, $R^1$ is T-Ar, T is a valence bond, Ar is a 5-7 membered saturated, partially unsaturated, or fully unsaturated monocyclic ring having 0-4 heteroatoms independently selected from nitrogen, oxygen, or sulfur, and Q is a $C_{1-6}$ alkylidene chain wherein the methylene unit attached to the nitrogen atom is replaced by C(O), then $R^2$ is other than optionally substituted phenyl; and when T is —NH—, —NHC(O)—, or —NHC(O)N(R)—, then $R^2$ is W—C(R)(W—Ar)$R^3$.

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$-$C_{12}$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-4 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, oxo, $N_3$, —$R^\circ$, —$OR^\circ$, —$SR^\circ$, 1,2-methylene-dioxy, 1,2-ethylenedioxy, protected OH (such as acyloxy), phenyl (Ph), Ph substituted with $R^\circ$, —O(Ph), O—(Ph) substituted with $R^\circ$, —$CH_2$(Ph), —$CH_2$(Ph) substituted with $R^\circ$, —$CH_2CH_2$(Ph), —$CH_2CH_2$(Ph) substituted with $R^\circ$, —$NO_2$, —CN, —$N(R^\circ)_2$, —$NR^\circ$ C(O)$R^\circ$, —$NR^\circ$C(O)N($R^\circ$)$_2$, —$NR^\circ CO_2R^\circ$, —$NR^\circ NR^\circ C(O)R^\circ$, —$NR^\circ NR^\circ$C(O)N($R^\circ$)$_2$, —$NR^\circ NR^\circ CO_2R^\circ$, —C(O)C(O)$R^\circ$, —C(O)$CH_2$C(O)$R^\circ$, —$CO_2R^\circ$, —C(O)$R^\circ$, —C(O)N($R^\circ$)$_2$, —OC(O)N($R^\circ$)$_2$, —S(O)$_2R^\circ$, —$SO_2$N($R^\circ$)$_2$, —S(O)$R^\circ$, —$NR^\circ SO_2$N($R^\circ$)$_2$, —$NR^\circ SO_2R^\circ$, —C(=S)N($R^\circ$)$_2$, —C(=NH)—N($R^\circ$)$_2$, or —$(CH_2)_y$NHC(O)$R^\circ$, wherein y is 0-4, each $R^\circ$ is independently selected from hydrogen, optionally substituted $C_{1-6}$ aliphatic, an unsubstituted 5-6 membered heteroaryl or heterocyclic ring having 0-4 heteroatoms independently selected from nitrogen, oxygen, or sulfur, phenyl (Ph), —O(Ph), or —$CH_2$(Ph)—$CH_2$(Ph). Substituents on the aliphatic group of $R^\circ$ are selected from $NH_2$, NH($C_{1-4}$ aliphatic), N($C_{1-4}$ aliphatic)$_2$, halogen, $C_{1-4}$ aliphatic, OH, O—($C_{1-4}$ aliphatic), $NO_2$, CN, $CO_2H$, $CO_2$($C_{1-4}$ aliphatic), —O(halo $C_{1-4}$ aliphatic), or halo $C_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Substituents on the aliphatic group of R* are selected from $NH_2$, NH($C_{1-4}$ aliphatic), N($C_{1-4}$ aliphatic)$_2$, halogen, $C_{1-4}$ aliphatic, OH, O—($C_{1-4}$ aliphatic), $NO_2$, CN, $CO_2H$, $CO_2$($C_{1-4}$ aliphatic), —O(halo $C_{1-4}$ aliphatic), or halo $C_{1-4}$ aliphatic.

Substituents on the nitrogen of a non-aromatic heterocyclic ring are selected from —$R^+$, —N($R^+$)$_2$, —C(O)$R^+$, —$CO_2R^+$, —C(O)C(O)$R^+$, —C(O)$CH_2$C(O)$R^+$, —$SO_2R^+$, —$SO_2N(R^+)_2$, —$C(=S)N(R^+)_2$, —$C(=NH)$—$N(R^+)_2$, or —$NR^+SO_2R^+$; wherein $R^+$ is hydrogen, an optionally substituted $C_{1-6}$ aliphatic, optionally substituted phenyl (Ph), optionally substituted —O(Ph), optionally substituted —$CH_2$(Ph), optionally substituted —$CH_2CH_2$(Ph), or an unsubstituted 5-6 membered heteroaryl or heterocyclic ring. Substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, O—($C_{1-4}$ aliphatic), $NO_2$, CN, $CO_2H$, $CO_2(C_{1-4}$ aliphatic), —O(halo $C_{1-4}$ aliphatic), or halo $C_{1-4}$ aliphatic.

The term "alkylidene chain" refers to a straight or branched carbon chain that may be fully saturated or have one or more units of unsaturation and has two points of connection to the rest of the molecule. That is, alkylidene refers to an aliphatic group (alkyl, alkenyl, or alkynyl) that has two points of connection to the rest of the molecule.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of this invention may exist in alternative tautomeric forms. Unless otherwise indicated, the representation of either tautomer is meant to include the other.

A preferred embodiment of this invention provides a compound wherein $R^2$ is —$C(R)(Ar)R^3$.

In another preferred embodiment, $R^2$ is —$C(R)(WAr)R_3$ (where R is preferably, H).

In other preferred embodiments, $R^2$ is as depicted in compounds I-6, I-7, I-12, or I-101-I-197.

This invention also provides compounds wherein the T moiety is T', wherein T' is —N(R)—, —N(R)C(O)—, —N(R)C(O)NH—, —N(R)CH$_2$—, or —N(R)SO$_2$—;

According to one embodiment, the T moiety of the $R^1$ group of formula I is selected from a valence bond, or a $C_{1-6}$ alkylidene chain wherein up to two methylene units of T are optionally, and independently, replaced by —O—, —S—, —C(O)N(R)—, —C(O)—, or —SO$_2$—. Examples of such groups include —CH$_2$—, —CH$_2$CH$_2$—, —CH=CH—, —C≡C—, —CH$_2$(CH$_3$)—, —SC(O)—, —CH$_2$C(O)—, —C(O)NH—, —OC(O)NH—, —O—, and —S—.

According to another embodiment, the T moiety of the $R^1$ group of formula I is selected from a valence bond, or a $C_{1-6}$ alkylidene chain wherein up to one methylene unit of T is optionally replaced by —N(R)—, —N(R)C(O)—, —N(R)C(O)N(R)—, —N(R)SO$_2$—, or —N(R)SO$_2$N(R)—. Examples of such groups include —NH—, —NHCH$_2$—, —NHC(O)—, —NHC(O)NH—, —NHC(O)CH$_2$—, and NHC(O)CH$_2$CH$_2$—. Further examples of such groups include —N(CH$_3$)—, —N(CH$_3$)CH$_2$—, —N(CH$_3$)C(O)—, and —N(CH$_3$)SO$_2$—.

Preferred T moieties of the T-Ar group of $R^1$ are selected from a valence bond, —N(R)C(O)—, —NH—, —NHCH$_2$—, —NHSO$_2$—, —CH$_2$NH—, —SC(O)—, —CH$_2$C(O)—, —C≡C—, —CH$_2$— or —CH$_2$CH$_2$—. More preferred T moieties of the T-Ar group of $R^1$ are selected from —NHC(O)—, —NH—, —NHCH$_2$—, —CH$_2$—, —C≡C—, or —CH$_2$CH$_2$—. Most preferred T moieties of the T-Ar group of $R^1$ are selected from —N(R)C(O)—, —NH—, or —NHCH$_2$—. In one embodiment, $R^1$ is -T-Ar, wherein T is —N(R)C(O)— and Ar is thienyl.

The when the Ar moiety of the $R_1$ group of formula I is an optionally substituted phenyl ring, preferred optional substituents, when present, are optionally substituted R°, phenyl, halogen, nitro, CN, OR°, SR°, N(R°)$_2$, SO$_2$R°, C(O)R°, C(O)OR, and C(O)N(R°)$_2$, wherein each R° is as defined supra. Examples of such groups include chloro, bromo, fluoro, CN, nitro, OMe, OPh, OCF$_3$, OCH$_2$Ph, OEt, SCHF$_2$, methyl, ethyl, isopropyl, propyl, vinyl, CF$_3$, acetylenyl, CH$_2$Ph, CH$_2$NH$_2$, CH$_2$N(Et)$_2$, CH$_2$morpholin-4-yl, CH$_2$piperdin-1-yl, CH$_2$imidazol-1-yl, CH$_2$piperazin-1-yl, C(O)NH$_2$, C(O)Me, SO$_2$Me, NHEt, and NHMe.

Preferred Ar moieties of the $R^1$ group of formula I are selected from an optionally substituted 5-6 membered saturated, partially unsaturated, or fully unsaturated monocyclic ring having 0-4 heteroatoms independently selected from nitrogen, oxygen, or sulfur. Examples of such Ar rings include optionally substituted phenyl, thienyl, furan, pyrimidinyl, and pyridyl rings. Preferred substituents on the Ar group, when present, include fluoro, CF$_3$, Me, Et, iPr, vinyl, acetylene, R°, Cl, nitro, CN, OMe, OPh, OCF$_3$, SO$_2$NH2, C(O)OEt, C(O)OH, CH$_2$CO$_2$H, CH$_2$CH$_2$CO$_2$H, CH$_2$NH$_2$ and C(O)NH$_2$, pyrrolidinyl, thienyl, oxazolyl, isoxazolyl, and tetrazolyl.

Preferred W groups of formula I are selected from a valence bond, —CH$_2$—, or —CH$_2$CH$_2$—.

When the $R^2$ group of formula I is Ar, preferred Ar groups are an optionally substituted ring selected from a 5-6 membered saturated, partially unsaturated, or fully unsaturated monocyclic ring having 0-4 heteroatoms independently selected from nitrogen, oxygen, or sulfur, or a 9-10 membered saturated, partially unsaturated, or fully unsaturated bicyclic ring having 0-4 heteroatoms independently selected from nitrogen, oxygen, or sulfur. Examples of such monocyclic rings include phenyl, pyridyl, pyrimidinyl, pyridonyl, furanyl, tetrazolyl, thienyl, cyclopentyl, cyclohexyl, and cycloheptyl. Examples of such bicyclic rings include benzo[1,3] dioxolyl, indan-1-onyl, naphthyl, benzothiophenyl, 2,3-dihydro-1H-isoindolyl, indanyl, benzofuranyl, and indolyl.

When present, preferred substituents on the Ar ring of the $R^2$ group of formula I include R°, halogen, oxo, OR°, phenyl, optionally substituted dialkylamino, haloalkyl, C(O)R°, NHC(O)R, or SR°. Examples of such preferred substituents include chloro, bromo, fluoro, OH, OMe, NHC(O)CH$_3$, OEt, C(O)phenyl, Ophenyl, N(CH$_2$CH$_2$Cl)$_2$, N(Me)$_2$, CF$_3$, and SCF$_3$. Other examples of preferred Ar groups of formula I also include those shown in Table 1 below.

When the $R^2$ group of formula I is W—C(R)(W—Ar)R$^3$, preferred $R^3$ groups include R', W—OR$^5$, W—N(R$^4$)$_2$, Ar$^1$, N(R)C(O)W—N(R$^4$)$_2$, and N(R)W—N(R$^4$)$_2$. Examples of such $R^3$ groups include CH$_2$OH, OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$CH$_2$N(Me)$_2$, CH$_2$C(Me)$_2$NH$_2$, CH$_2$C(Me)$_2$CHMe, NHCO$_2$t-butyl, phenyl, cyclopentyl, methyl, ethyl, isopropyl, cyclopropyl, NH(CH$_2$)$_3$NH$_2$, NH(CH$_2$)$_2$NH$_2$, NH (CH$_2$)$_2$NHEt, NHCH$_2$pyridyl, NHSO$_2$phenyl, NHC(O)CH$_2$C(O)Ot-butyl, NHC(O)CH$_2$NH$_3$, NHCH$_2$-imidazol-4-yl, and also CH$_2$CH$_2$OH.

More preferably, the R$^3$ group of formula I is selected from OH, NH$_2$, CH$_2$NH$_2$, CH$_2$NHMe, CH$_2$N(Me)$_2$, CH$_2$CH$_2$NH$_2$, CH$_2$CH$_2$NHMe, CH$_2$CH$_2$N(Me)$_2$, CH$_2$C(Me)$_2$NH$_2$, CH$_2$C(Me)$_2$CHMe, NHCO$_2$t-butyl, phenyl, NH(CH$_2$)$_3$NH$_2$, NH(CH$_2$)$_2$NH$_2$, NH(CH$_2$)$_2$NHEt, NHCH$_2$pyridyl, NHSO$_2$phenyl, NHC(O)CH$_2$C(O)Ot-butyl, NHC(O)CH$_2$NH$_3$, and NHCH$_2$-imidazol-4-yl. Other more preferred R$^3$ groups of formula I are CH$_2$OH and CH$_2$CH$_2$OH.

Most preferably, the R$^3$ group of formula I is CH$_2$CH$_2$NH$_2$. Other most preferred R$^3$ groups of formula I are CH$_2$OH, CH$_2$CH$_2$OH, and CH$_2$NH$_2$.

Preferred rings formed by the R and R$^3$ moieties of the W—C(R)(W—Ar)R$^3$ group of R$^2$ are selected from a 5-6 membered saturated ring having 0-2 heteroatoms independently selected from nitrogen, oxygen, or sulfur. Examples of such rings formed by R and R$^3$ include piperidinyl, pyrrolidinyl, piperazinyl, morpholinyl, and thiomorpholinyl.

When the R$^2$ group of formula I is W—C(R)(W—Ar)R$^3$, preferred Ar groups of the W—C(R)(W—Ar)R$^3$ moiety are selected from an optionally substituted 5-6 membered saturated, partially unsaturated, or fully unsaturated monocyclic ring having 0-4 heteroatoms independently selected from nitrogen, oxygen, or sulfur, or an optionally substituted 9-10 membered saturated, partially unsaturated, or fully unsaturated bicyclic ring having 0-4 heteroatoms independently selected from nitrogen, oxygen, or sulfur. Examples of such monocyclic rings include phenyl, pyridyl, furanyl, pyridone, and thienyl. Examples of such bicyclic rings include benzo[1,3]dioxolyl, naphthyl, indanyl, and indolyl. When present, preferred substituents on the Ar ring of the W—C(R)(W—Ar)R$^3$ group of R$^2$ include R$^o$, halogen, OR$^o$, phenyl, N(R$^o$)$_2$, NHC(O)R$^o$, or SR$^o$. Examples of such groups include fluoro, chloro, bromo, CF$_3$, OH, OMe, OPh, OCH$_2$Ph, SMe, NH$_2$, NHC(O)Me, methyl, ethyl, isopropyl, isobutyl, and cyclopropyl.

According to another embodiment, R$^3$ is —W—OR$^5$. W, in this embodiment, is preferably a C1, C2, or C3 alkyl group (preferably a C1 or C2 alkyl). R$^5$, in these embodiments, is preferably H thus forming a hydroxy group (or an appropriate derivative thereof).

According to yet another embodiment, R$^3$ is —W—N(R$^4$)$_2$. W, in this embodiment, is preferably a C1, C2, or C3 alkyl group (preferably a C1 alkyl). One or both R$^4$ groups, in these embodiments, is preferably H thus forming a secondary or tertiary amino group (or an appropriate derivative thereof).

According to another embodiment, the present invention relates to a compound of formula II:

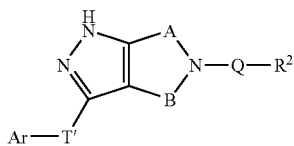

II or a pharmaceutically acceptable salt thereof, wherein:
A is —CH$_2$— or —CH$_2$C(R$^a$)(R$^b$)—, wherein:
  R$^a$ and R$^b$ are independently hydrogen, an optionally substituted C$_{1-6}$ aliphatic group, or halogen, or R$^a$ and R$^b$ are taken together to form a 3-6 membered saturated or partially unsaturated ring having 0-2 heteroatoms independently selected from nitrogen, oxygen or sulfur;

B is A is —CH$_2$— or —CH$_2$C(R$^c$)(R$^d$)—, wherein:
  R$^c$ and R$^d$ are independently hydrogen, C$_{1-4}$ aliphatic, or halogen, or R$^c$ and R$^d$ are taken together to form a cyclopropyl ring;
R$^1$ is T'-Ar;
T' is —N(R')—, —N(R')C(O)—, —N(R')C(O)NH—, —N(R')CH$_2$—, or —N(R')SO$_2$—;
each R is independently selected from hydrogen or an optionally substituted C$_{1-6}$ aliphatic group, or:
  two R groups on the same nitrogen, taken together with the nitrogen atom attached thereto, form a 5-7 membered saturated, partially unsaturated, or aromatic ring having 1-3 heteroatoms independently selected from nitrogen, oxygen, or sulfur;
Q is a valence bond or a C$_{1-6}$ alkylidene chain, wherein up to two methylene units of Q are optionally, and independently, replaced by —O—, —N(R)—, —S—, —N(R)C(O)—, —C(O)N(R)—, —C(O)—, or —SO$_2$—;
R$^2$ is selected from Ar, R$^3$, or C(R)(Ar)R$^3$, wherein:
  R and R$^3$ optionally form a 5-7 membered saturated or partially unsaturated ring having 0-4 heteroatoms independently selected from nitrogen, oxygen, or sulfur;
  each Ar is independently an optionally substituted ring selected from a 5-7 membered saturated, partially unsaturated, or fully unsaturated monocyclic ring having 0-4 heteroatoms independently selected from nitrogen, oxygen, or sulfur, or an 8-10 membered saturated, partially unsaturated, or fully unsaturated bicyclic ring having 0-4 heteroatoms independently selected from nitrogen, oxygen, or sulfur;
  each R$^3$ is independently selected from R', Ar$^1$, W—OR$^5$, W—OC(O)R$^5$, W—CONHR$^5$, W—OC(O)NHR$^5$, W—SR$^5$, W—N(R$^4$)$_2$, N(R)(W—Ar), N(R)C(O)W—N(R$^4$)$_2$, or N(R)W—N(R$^4$)$_2$, wherein:
    each W is independently a valence bond or a C$_{1-6}$ alkylidene chain;
  R' is an optionally substituted C$_{1-6}$ aliphatic group;
  each Ar$^1$ is independently selected from an optionally substituted 5-7 membered saturated, partially unsaturated, or fully unsaturated monocyclic ring having 0-4 heteroatoms independently selected from nitrogen, oxygen, or sulfur;
  each R$^4$ is independently selected from R, COR$^5$, CO$_2$R$^5$, CON(R$^5$)$_2$, SO$_2$R$^5$, SO$_2$N(R$^5$)$_2$, or Ar$^1$; and
  each R$^5$ is independently selected from R or Ar.
Preferred A, B, Ar, Q, and R$^2$ groups of formula II are those described above for compounds of formula I. Preferred T' groups of formula II are selected from —N(R')—, —N(R')C(O)—, —N(R')C(O)NH—, —N(R')CH$_2$—, or —N(R')SO$_2$— (wherein R' is R). More preferred T' groups of formula II are selected from —N(R')C(O)—, —N(R')—, —N(R')CH$_2$—, —N(R')SO$_2$— (wherein R' is R.

According to another embodiment, the present invention relates to a compound of formula III:

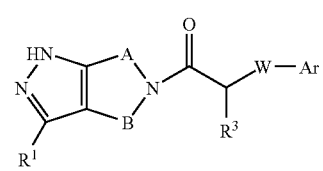

III or a pharmaceutically acceptable salt thereof, wherein:
A is —CH$_2$— or —CH$_2$C(R$^a$)(R$^b$)—, wherein:
  R$^a$ and R$^b$ are independently hydrogen, an optionally substituted C$_{1-6}$ aliphatic group, or halogen, or R$^a$ and R$^b$ are taken together to form a 3-6 membered saturated or partially unsaturated ring having 0-2 heteroatoms independently selected from nitrogen, oxygen or sulfur;

B is A is —CH₂— or —CH₂C(R$^c$)(R$^d$)—, wherein:
R$^c$ and R$^d$ are independently hydrogen, $C_{1-4}$ aliphatic, or halogen, or R$^c$ and R$^d$ are taken together to form a cyclopropyl ring;

R$^1$ is T-Ar;

each T is independently selected from a valence bond or a $C_{1-6}$ alkylidene chain, wherein up to two methylene units of T are optionally, and independently, replaced by —O—, —N(R)—, —S—, —N(R)C(O)—, —C(O)N(R)—, —C(O)—, or —SO₂—;

each R is independently selected from hydrogen or an optionally substituted $C_{1-6}$ aliphatic group, or:
two R groups on the same nitrogen, taken together with the nitrogen atom attached thereto, form a 5-7 membered saturated, partially unsaturated, or aromatic ring having 1-3 heteroatoms independently selected from nitrogen, oxygen, or sulfur;

each Ar is independently an optionally substituted ring selected from a 5-7 membered saturated, partially unsaturated, or fully unsaturated monocyclic ring having 0-4 heteroatoms independently selected from nitrogen, oxygen, or sulfur, or an 8-10 membered saturated, partially unsaturated, or fully unsaturated bicyclic ring having 0-4 heteroatoms independently selected from nitrogen, oxygen, or sulfur;

each R$^3$ is independently selected from R', Ar$^1$, W—OR$^5$, W—OC(O)R$^5$, W—CONHR$^5$, W—OC(O)NHR$^5$, W—SR$^5$, W—N(R$^4$)₂, N(R)(W—Ar), N(R)C(O)W—N(R$^4$)₂, or N(R)W—N(R$^4$)₂, wherein:
each W is independently a valence bond or a $C_{1-6}$ alkylidene chain;

R' is an optionally substituted $C_{1-6}$ aliphatic group;

each Ar$^1$ is independently selected from an optionally substituted 5-7 membered saturated, partially unsaturated, or fully unsaturated monocyclic ring having 0-4 heteroatoms independently selected from nitrogen, oxygen, or sulfur;

each R$^4$ is independently selected from R, COR$^5$, CO₂R$^5$, CON(R$^5$)₂, SO₂R$^5$, SO₂N(R$^5$)₂, or Ar$^1$; and each R$^5$ is independently selected from R or Ar.

Preferred R$^1$ groups of formula III include those described above for compounds of formula I.

Preferred Ar groups of formula III include an optionally substituted ring selected from a 5-6 membered saturated, partially unsaturated, or fully unsaturated monocyclic ring having 0-4 heteroatoms independently selected from nitrogen, oxygen, or sulfur, or a 9-10 membered saturated, partially unsaturated, or fully unsaturated bicyclic ring having 0-4 heteroatoms independently selected from nitrogen, oxygen, or sulfur. Examples of such monocyclic rings include phenyl, pyridyl, thienyl, furanyl, cyclopentyl, cyclohexyl, and cycloheptyl. Examples of such bicyclic rings include benzo[1,3]dioxolyl, indan-1-onyl, naphthyl, benzothiophenyl, 2,3-dihydro-1H-isoindolyl, indanyl, benzofuranyl, and indolyl. When present, preferred substituents on the Ar group of formula III include R$^o$, halogen, OR$^o$, phenyl, optionally substituted dialkylamino, haloalkyl, C(O)R$^o$, or SR$^o$. Examples of such preferred substituents include tetrazolyl, oxazolyl, isoxazolyl, chloro, bromo, fluoro, OH, OMe, OEt, C(O)phenyl, Ophenyl, N(CH₂CH₂Cl)₂, N(Me)₂, CF₃, and SCF₃.

Preferred R$^3$ groups of formula III include R', Q-OR$^5$, Q-N(R$^4$)₂, Ar$^1$, N(R)C(O)Q-N(R$^4$)₂, and N(R)Q-N(R$^4$)₂. Examples of such R$^3$ groups include CH₂OH, OH, NH₂, CH₂NH₂, CH₂NHMe, CH₂N(Me)₂, CH₂CH₂NH₂, CH₂CH₂NHMe, CH₂C(Me)₂NH₂, CH₂C(Me)₂CHMe, CH₂CH₂N(Me)₂, CH₂CH₂NH₂, NHCO₂t-butyl, phenyl, cyclopentyl, methyl, ethyl, isopropyl, cyclopropyl, NH(CH₂)₃NH₂, NH(CH₂)₂NH₂, NH(CH₂)₂NHEt, NHCH₂pyridyl, NHSO₂phenyl, NHC(O)CH₂C(O)Ot-butyl, NHC(O)CH₂NH₃, and NHCH₂-imidazol-4-yl. Another examples of such R$^3$ groups include CH₂CH₂OH.

More preferably, the R$^3$ group of formula III is selected from OH, NH₂, CH₂NH₂, CH₂NHMe, CH₂N(Me)₂, CH₂CH₂NH₂, CH₂CH₂NHMe, CH₂CH₂N(Me)₂, CH₂C(Me)₂NH₂, CH₂C(Me)₂CHMe, NHCO₂t-butyl, phenyl, NH(CH₂)₃NH₂, NH(CH₂)₂NH₂, NH(CH₂)₂NHEt, NHCH₂pyridyl, NHSO₂phenyl, NHC(O)CH₂C(O)Ot-butyl, NHC(O)CH₂NH₃, and NHCH₂-imidazol-4-yl. Other more preferred R$^3$ groups of formula III are CH₂OH and CH₂CH₂OH.

Most preferably, the R$^3$ group of formula III is selected from CH₂CH₂NH₂.

According to another embodiment, the present invention relates to a compound of formula IV:

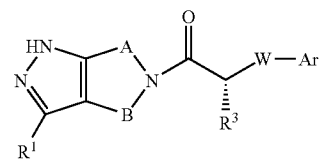

IV or a pharmaceutically acceptable salt thereof, wherein A, B, R$^1$, R$^3$, W, and Ar are as defined above for compounds of formula I. Preferred A, B, R$^1$, R$^3$, W, and Ar groups of formula IV are those set forth above for compounds of formula I.

According to another embodiment, the present invention relates to a compound of formula V:

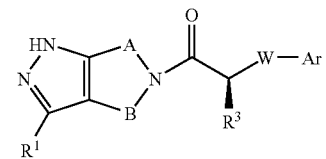

V or a pharmaceutically acceptable salt thereof, wherein A, B, R$^1$, R$^3$, W, and Ar are as defined above for compounds of formula I. Preferred A, B, R$^1$, R$^3$, W, and Ar groups of formula V are those set forth above for compounds of formula I.

According to one embodiment, the present invention relates to a compound of formula I, wherein A and B are each —CH₂—.

According to another embodiment, the present invention relates to a compound of formula II, wherein A and B are each —CH₂—.

According to another embodiment, the present invention relates to a compound of formula III, wherein A and B are each —CH₂—.

According to yet another embodiment, the present invention relates to a compound of formula IV, wherein A and B are each —CH₂—.

According to another embodiment, the present invention relates to a compound of formula V, wherein A and B are each —CH₂—.

According to one embodiment, the present invention relates to a compound of formula I, wherein A and B are each —CH$_2$CH$_2$—.

According to another embodiment, the present invention relates to a compound of formula II, wherein A and B are each —CH$_2$CH$_2$—.

According to another embodiment, the present invention relates to a compound of formula III, wherein A and B are each —CH$_2$CH$_2$—.

According to yet another embodiment, the present invention relates to a compound of formula IV, wherein A and B are each —CH$_2$CH$_2$—.

According to another embodiment, the present invention relates to a compound of formula V, wherein A and B are each —CH$_2$CH$_2$—.

According to one embodiment, the present invention relates to a compound of formula I, wherein one of A or B is —CH$_2$— and the other of A or B is —CH$_2$CH$_2$—.

According to another embodiment, the present invention relates to a compound of formula II, wherein one of A or B is —CH$_2$— and the other of A or B is —CH$_2$CH$_2$—.

According to another embodiment, the present invention relates to a compound of formula III, wherein one of A or B is —CH$_2$— and the other of A or B is —CH$_2$CH$_2$—.

According to yet another embodiment, the present invention relates to a compound of formula IV, wherein one of A or B is —CH$_2$— and the other of A or B is —CH$_2$CH$_2$—.

According to another embodiment, the present invention relates to a compound of formula V, wherein one of A or B is —CH$_2$— and the other of A or B is —CH$_2$CH$_2$—.

Representative compounds of formula I are set forth in Table 1 below.

TABLE 1

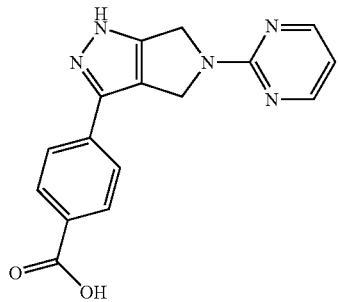

I-1

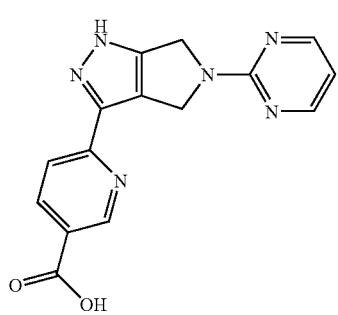

I-2

TABLE 1-continued

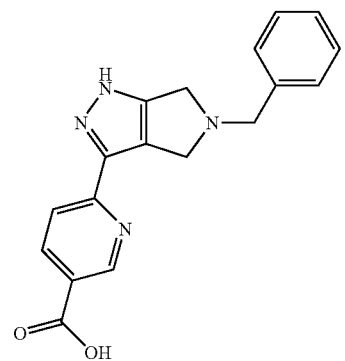

I-3

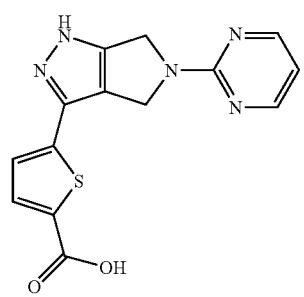

I-4

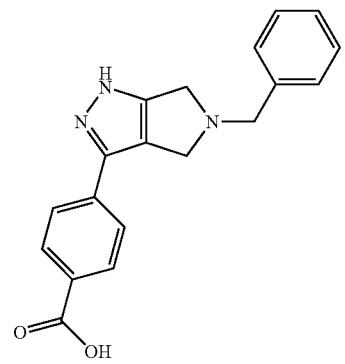

I-5

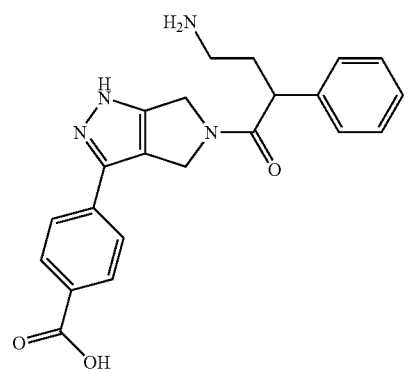

I-6

TABLE 1-continued
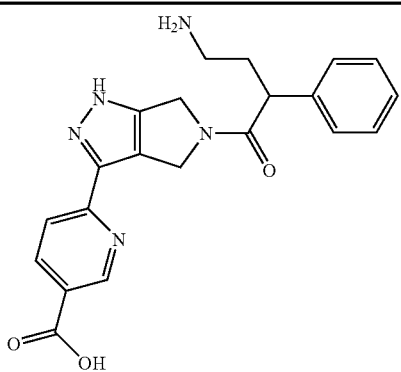
I-7
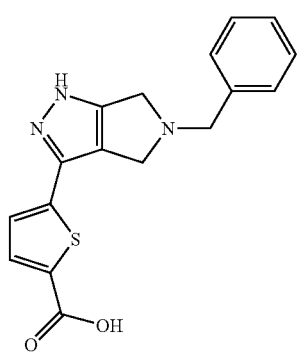
I-8
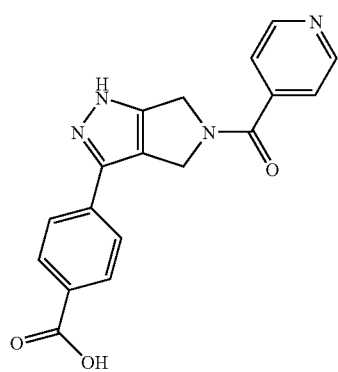
I-9
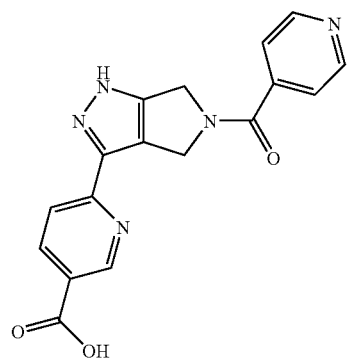
I-10
TABLE 1-continued
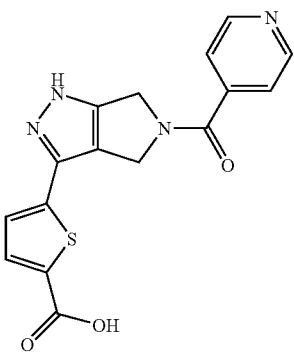
I-11
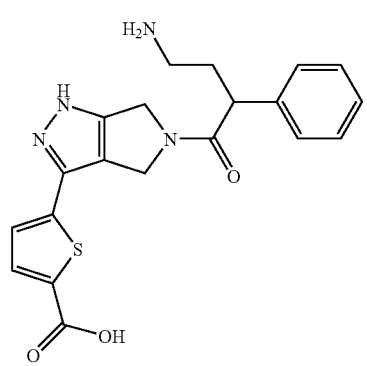
I-12
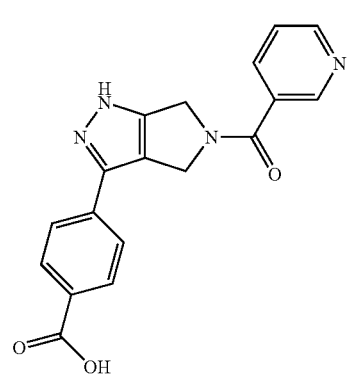
I-13
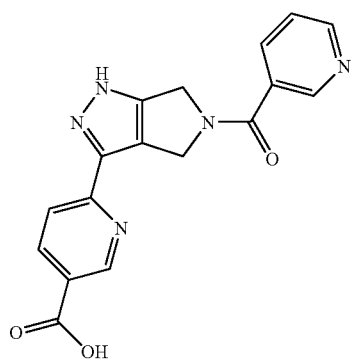
I-14

TABLE 1-continued
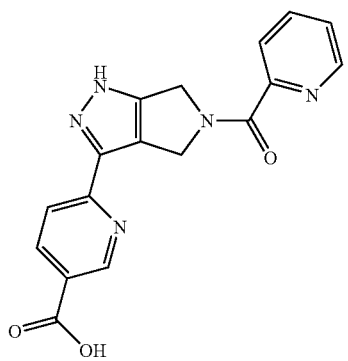
I-15
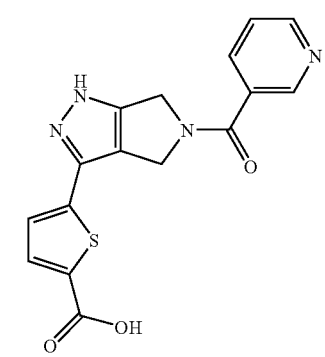
I-16
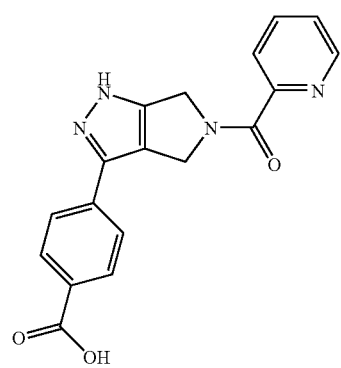
I-17
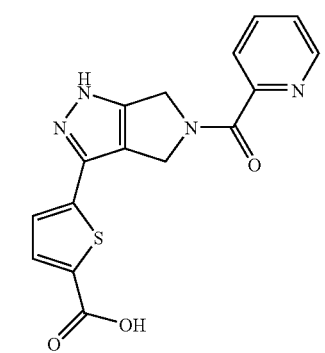
I-18
TABLE 1-continued
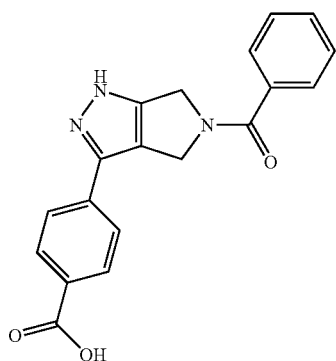
I-19
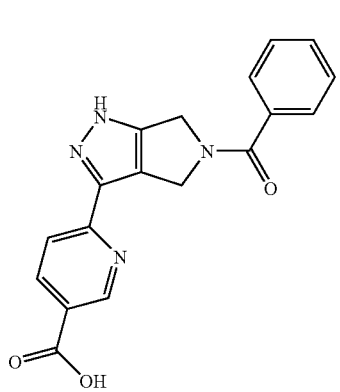
I-20
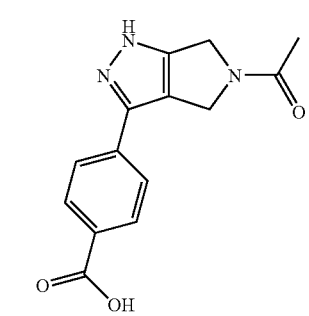
I-21
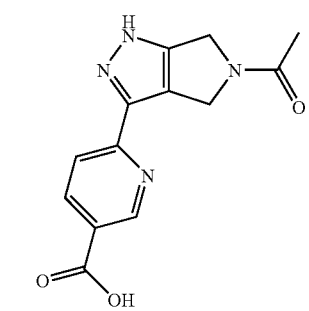
I-22

TABLE 1-continued
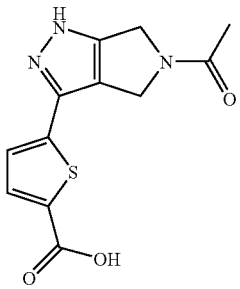
I-23
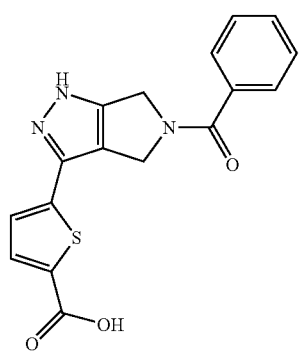
I-24
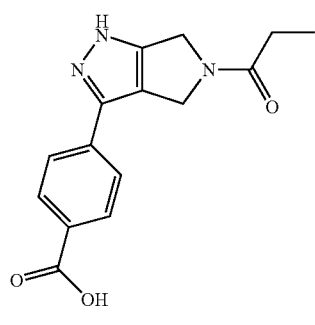
I-25
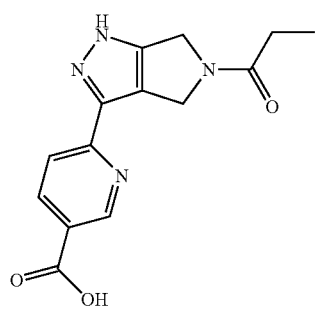
I-26
TABLE 1-continued
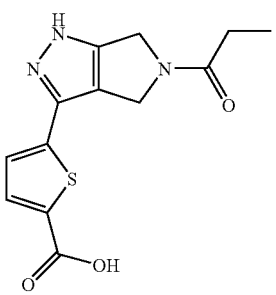
I-27
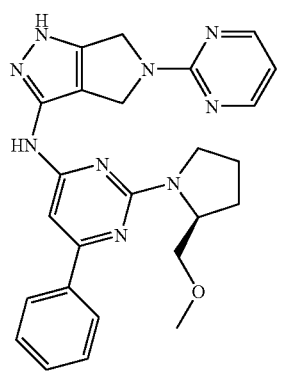
I-28
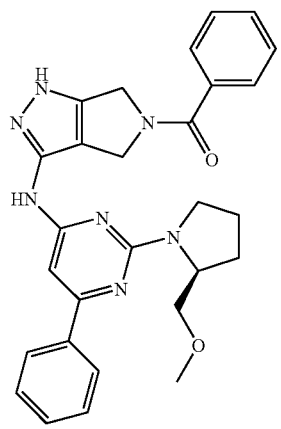
I-29

TABLE 1-continued
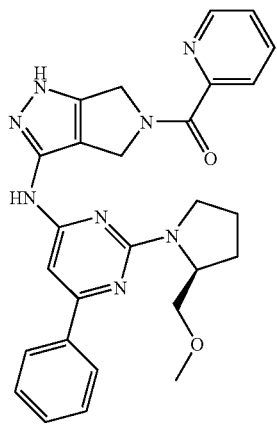
I-30
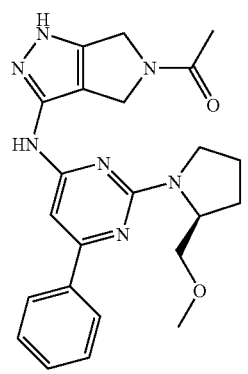
I-31
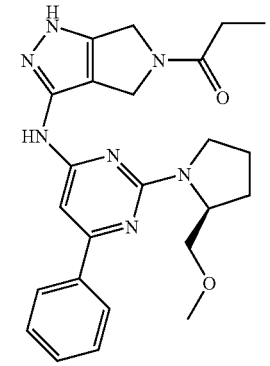
I-32
TABLE 1-continued
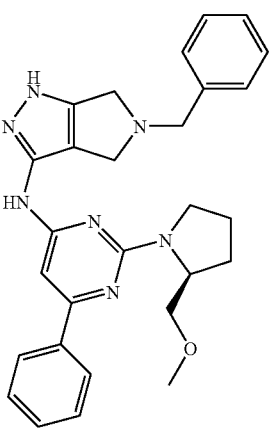
I-33
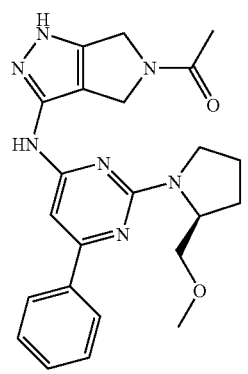
I-34
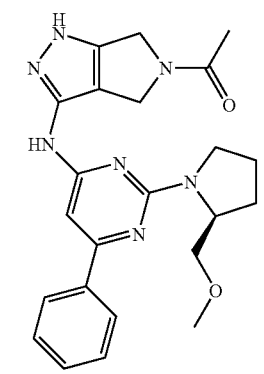
I-35

TABLE 1-continued
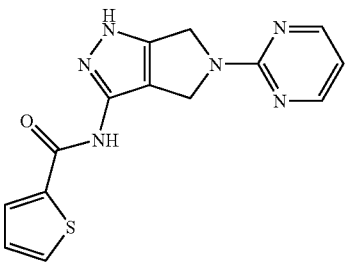
I-36
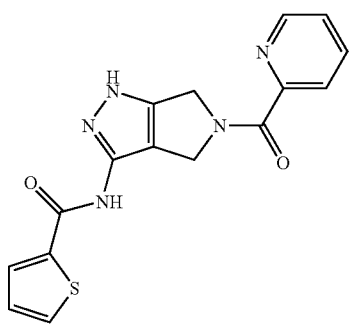
I-37
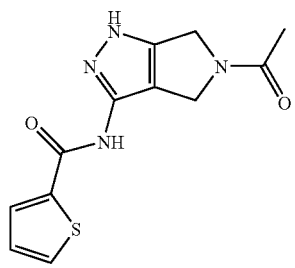
I-38
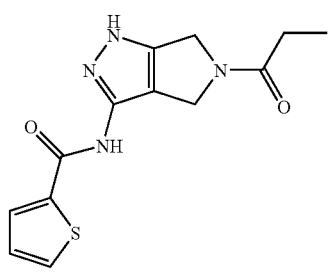
I-39
TABLE 1-continued
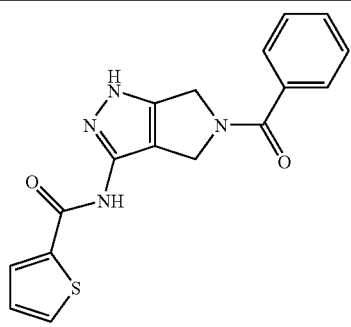
I-40
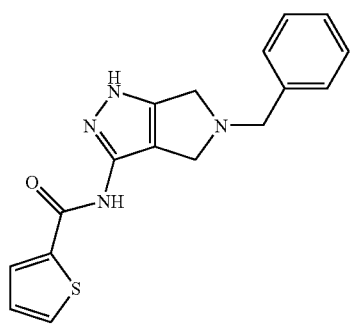
I-41
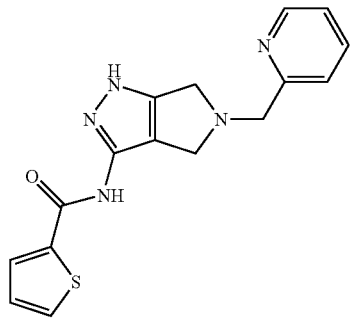
I-42
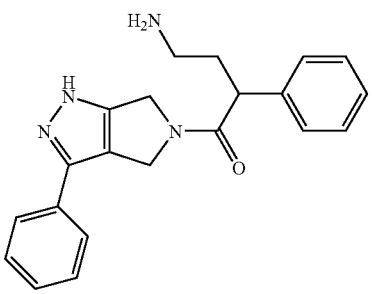
I-101

TABLE 1-continued
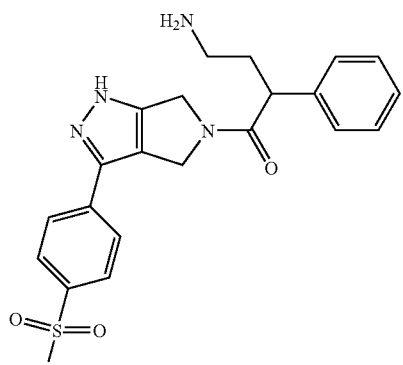
I-102
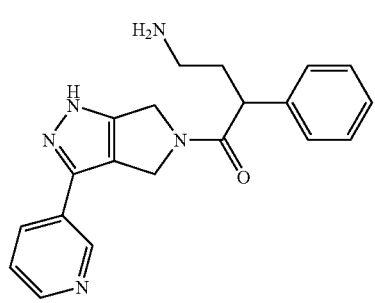
I-103
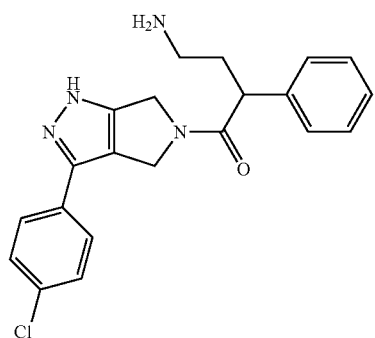
I-104
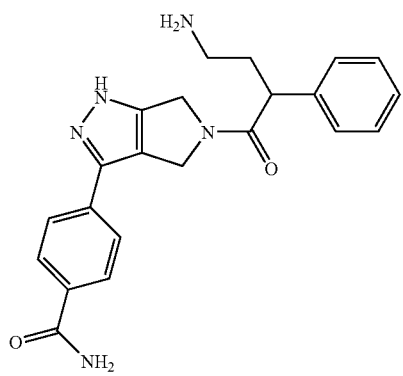
I-105
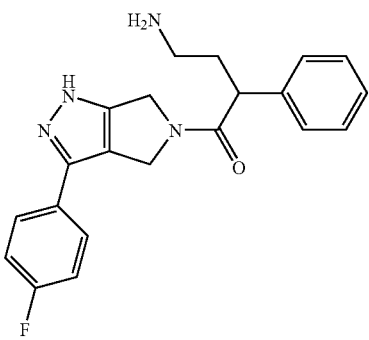
I-106
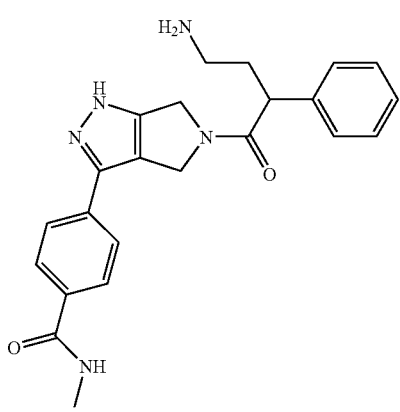
I-107
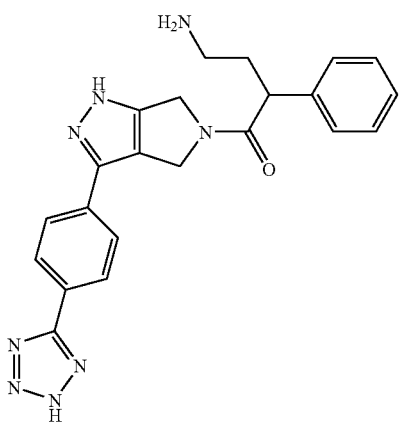
I-108

TABLE 1-continued
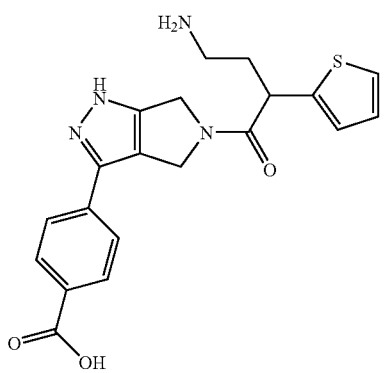
I-109
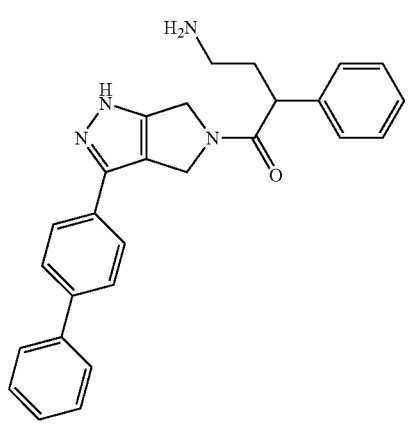
I-110
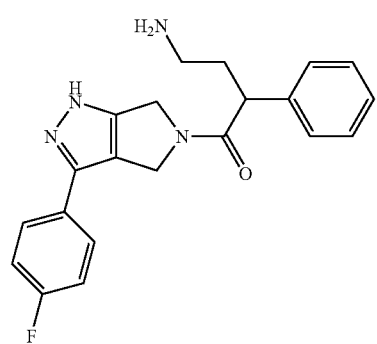
I-111
TABLE 1-continued
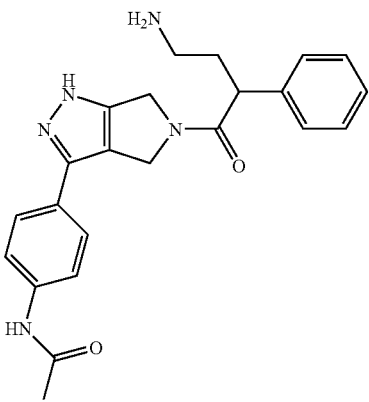
I-112
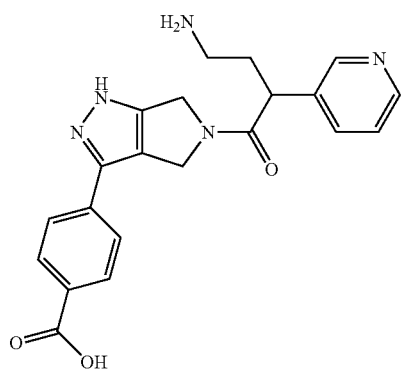
I-113
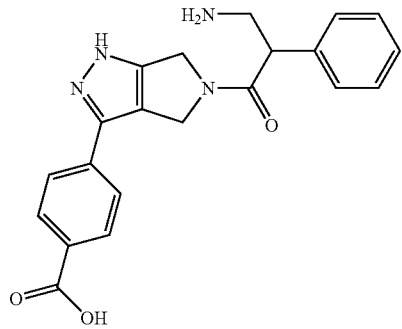
I-114
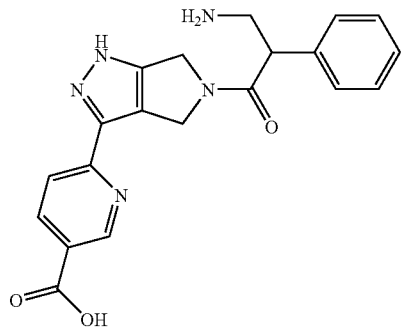
I-115

TABLE 1-continued
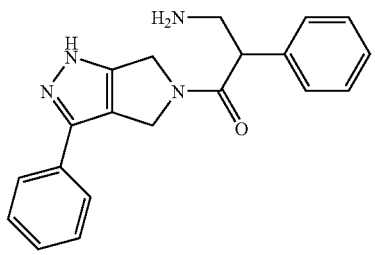
I-116
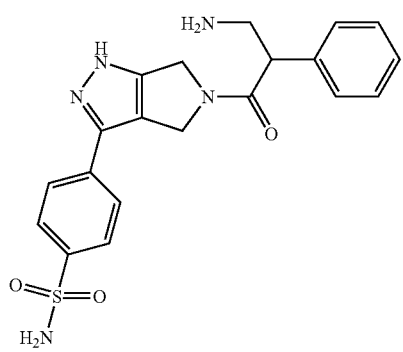
I-117
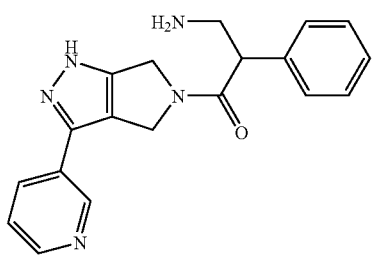
I-118
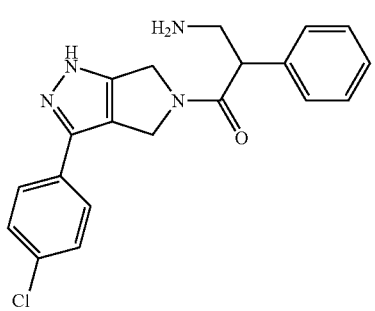
I-119
TABLE 1-continued
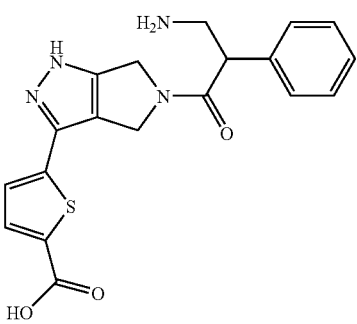
I-120
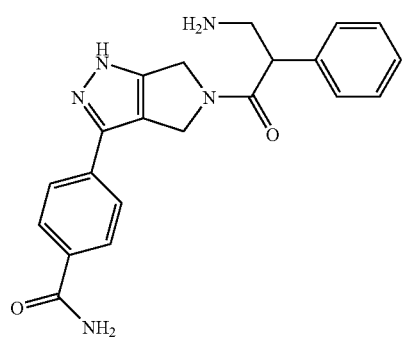
I-121
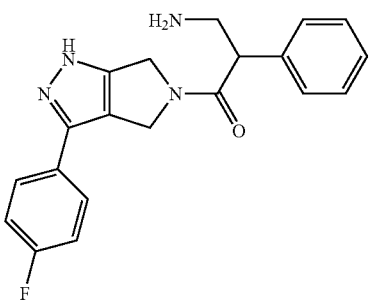
I-122
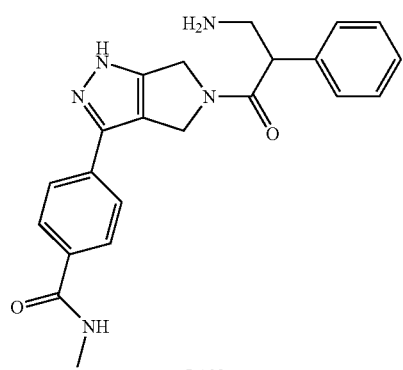
I-123

TABLE 1-continued
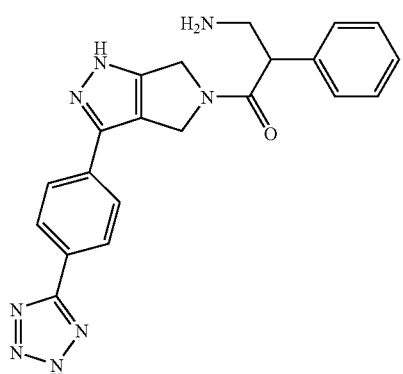
I-124
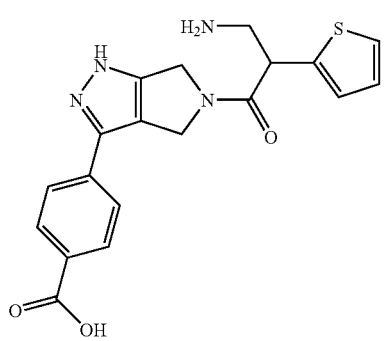
I-125
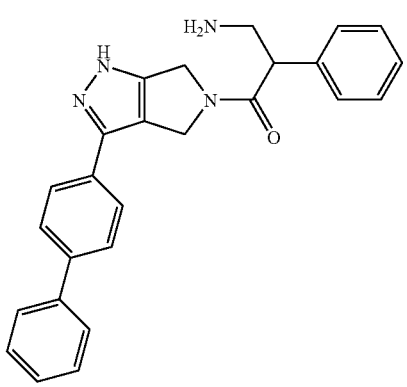
I-126
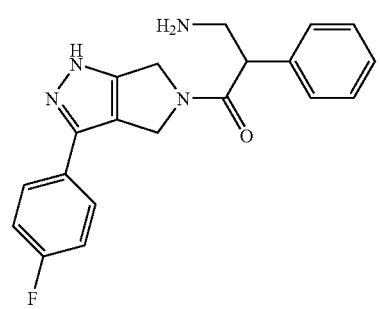 [SMILES: NCC(C(=O)N1Cc2[nH]nc(-c3ccccc3)c2C1)c1ccccc1]
I-127
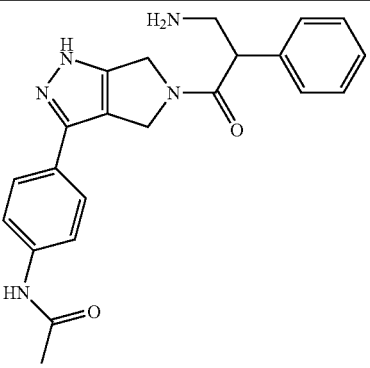
I-128
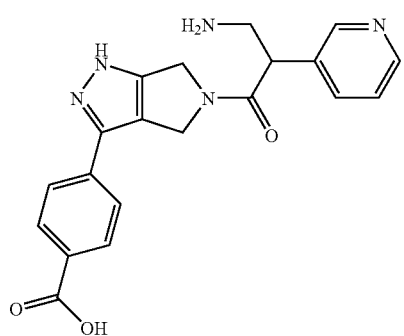
I-129
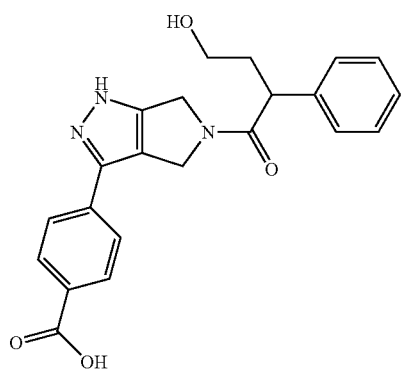
I-130
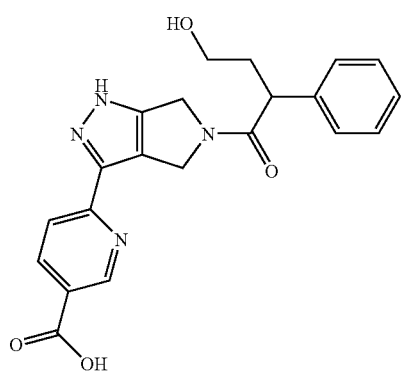
I-131

TABLE 1-continued
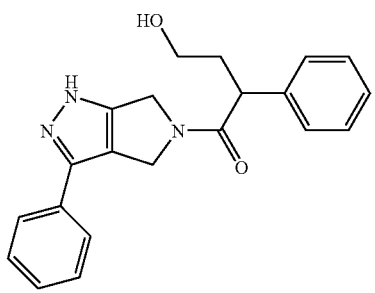
I-132
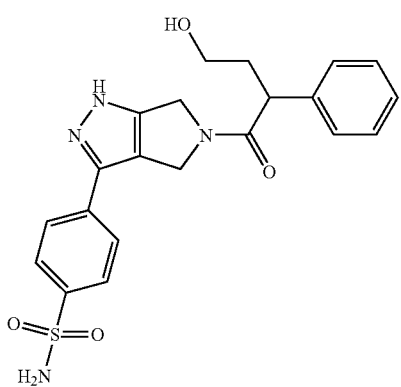
I-133
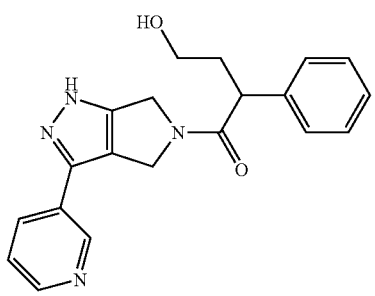
I-134
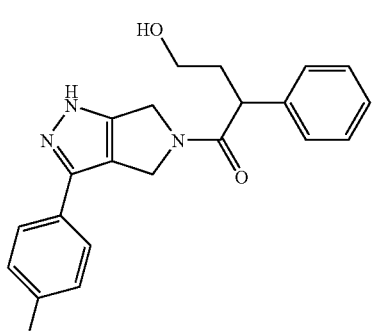
I-135
TABLE 1-continued
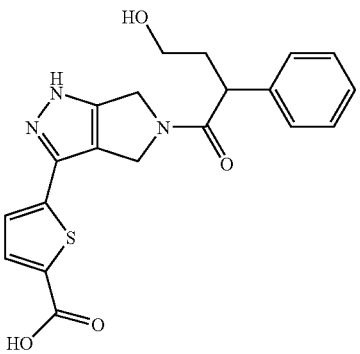
I-136
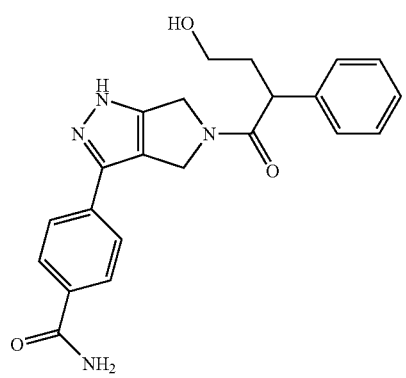
I-137
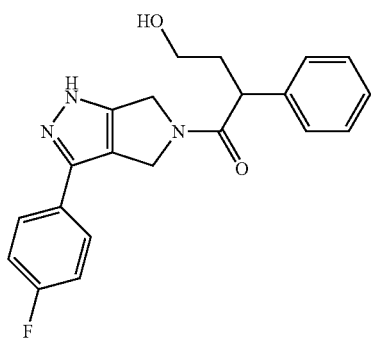
I-138
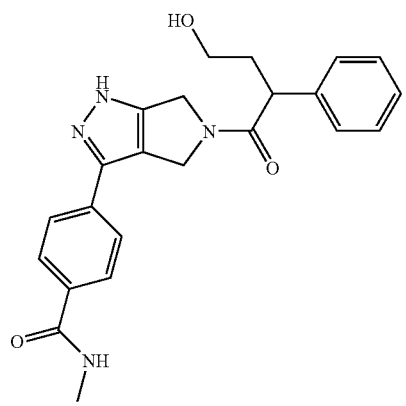
I-139

TABLE 1-continued
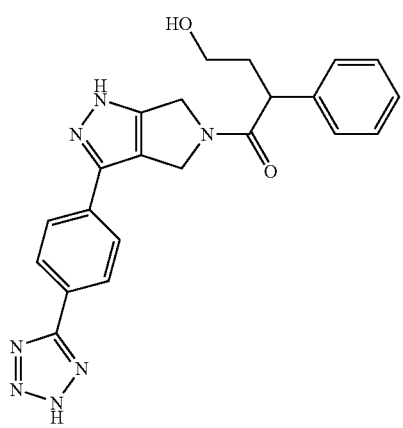
I-140
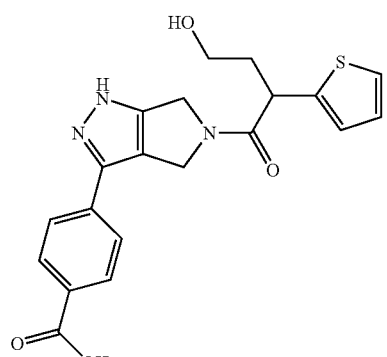
I-141
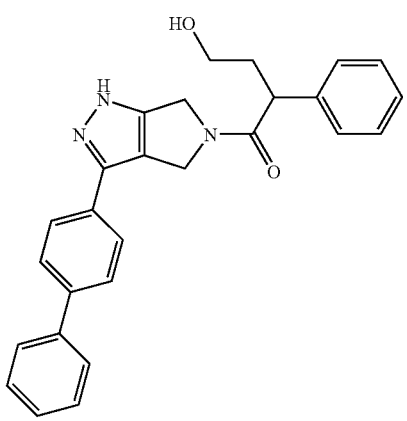
I-142
TABLE 1-continued
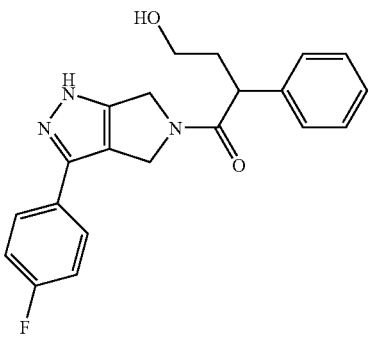 [SMILES: O=C(C(CCO)c1ccccc1)N1Cc2[nH]nc(-c3ccccc3)c2C1]
I-143
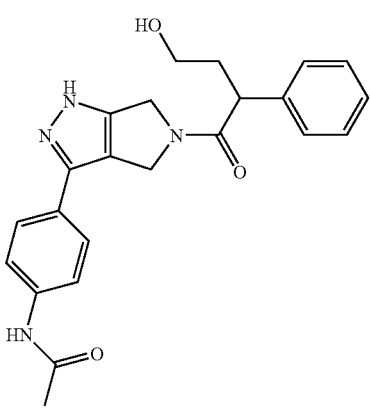
I-144
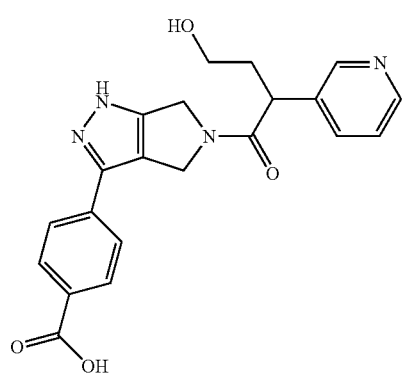
I-145
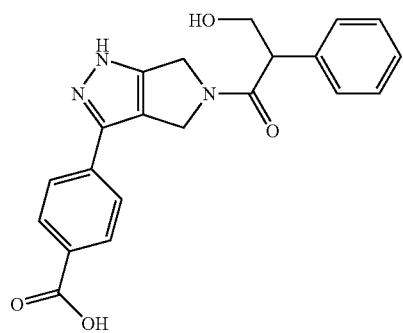
I-146

TABLE 1-continued
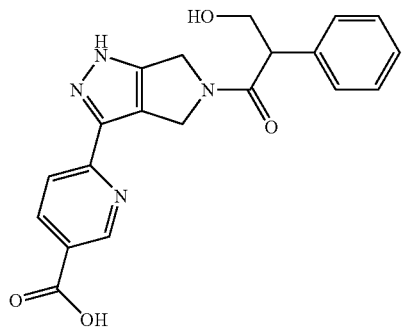
I-147
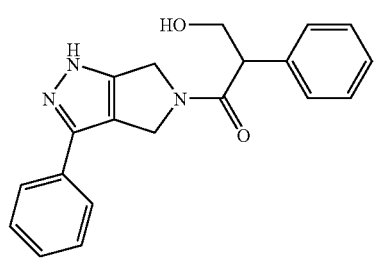
I-148
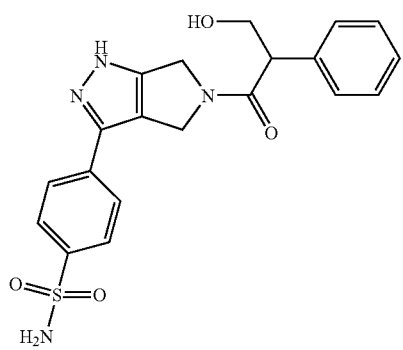
I-149
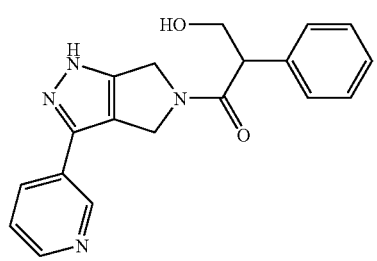
I-150
TABLE 1-continued
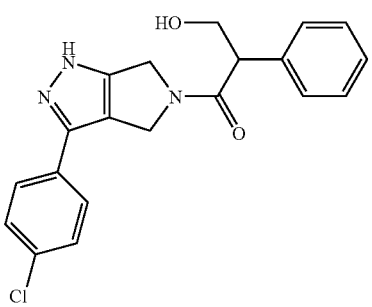
I-151
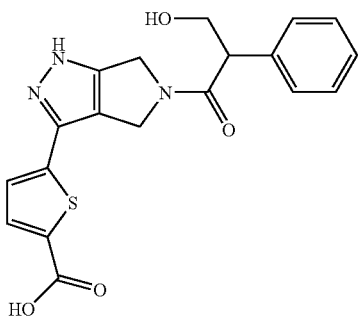
I-152
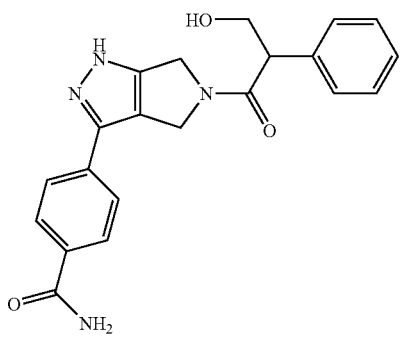
I-153
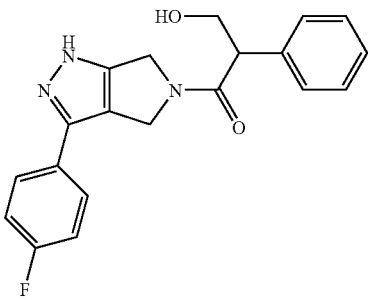
I-154

TABLE 1-continued
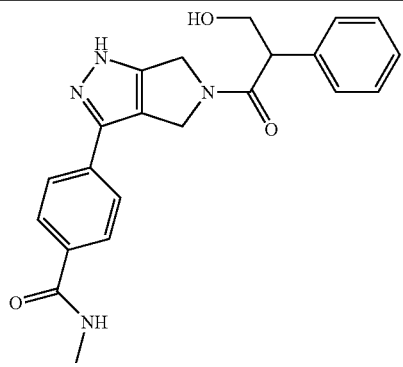
I-155
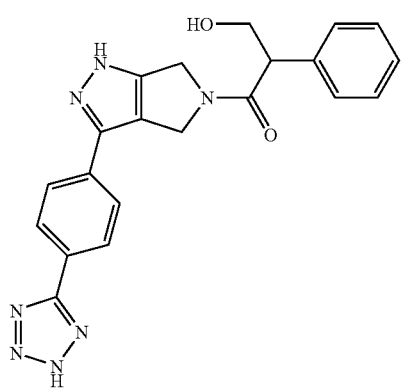
I-156
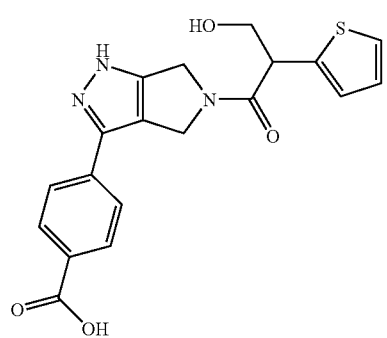
I-157
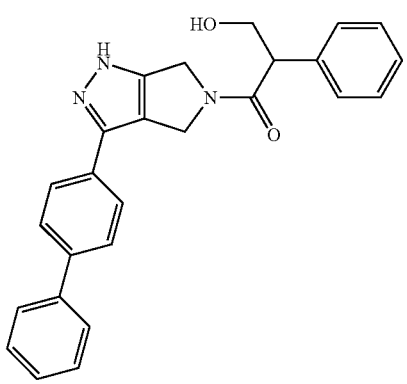
I-158
TABLE 1-continued
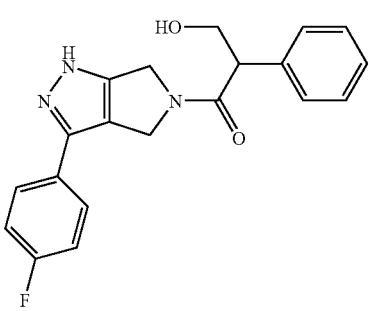
I-159
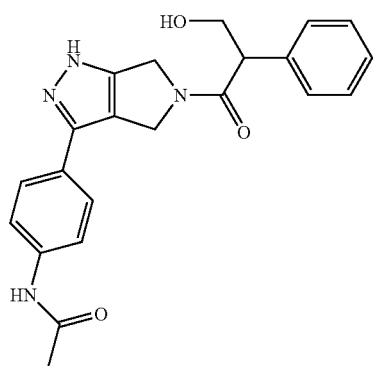
I-160
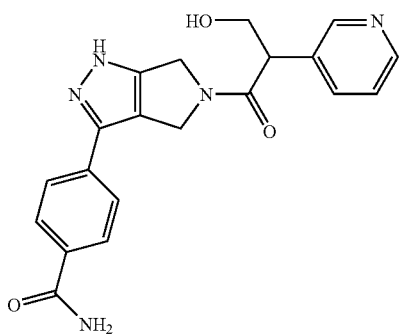
I-161
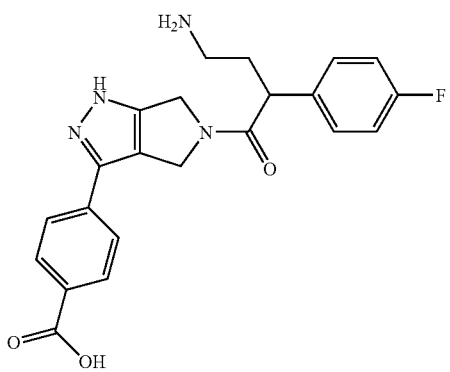
I-162

TABLE 1-continued
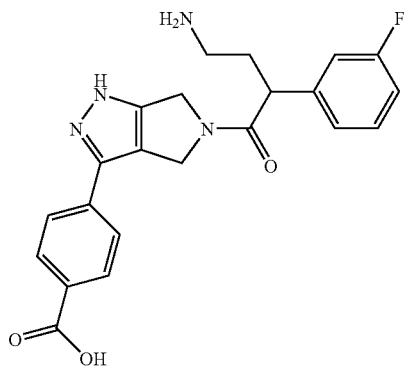
I-163
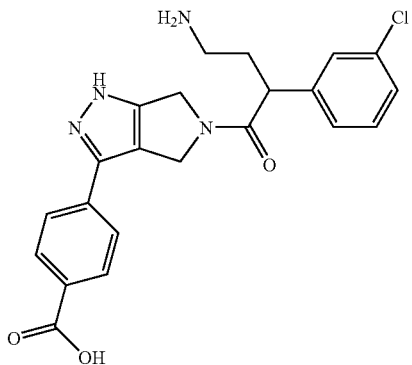
I-166
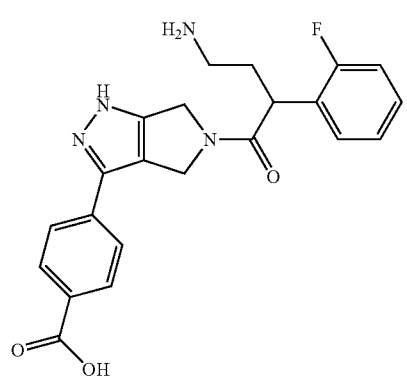
I-164
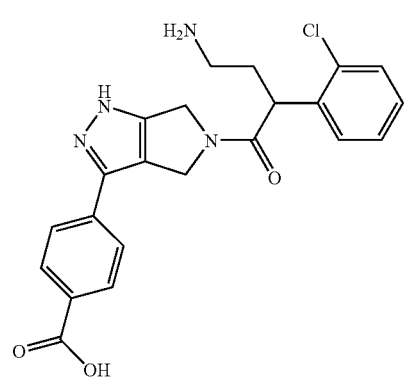
I-167
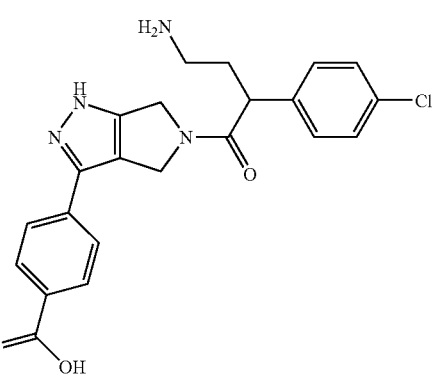
I-165
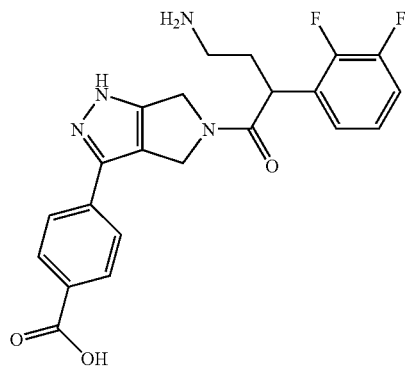
I-168

TABLE 1-continued
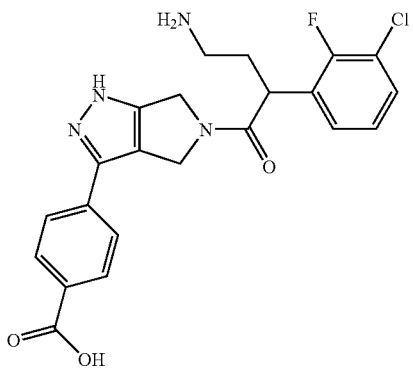
I-169
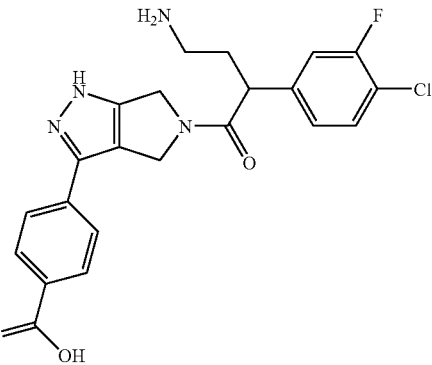
I-172
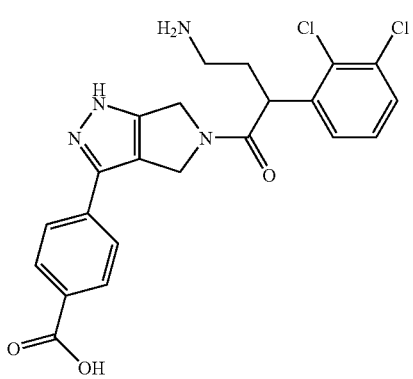
I-170
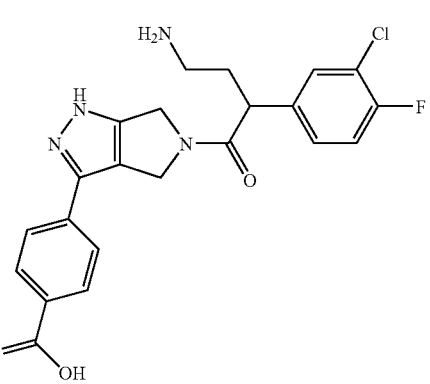
I-173
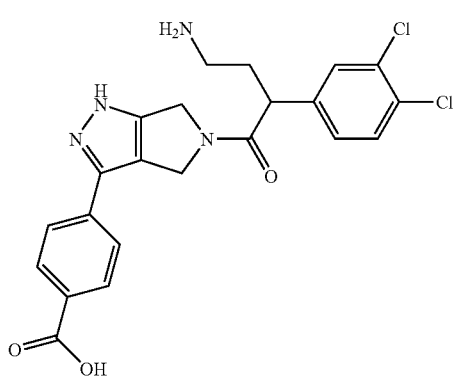
I-171
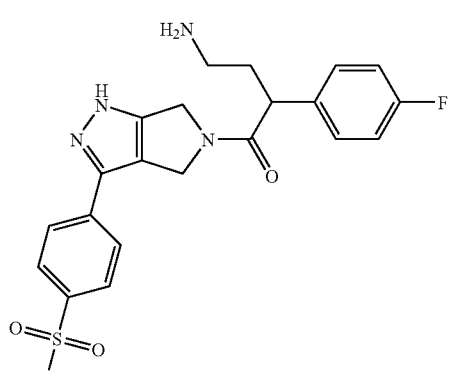
I-174

TABLE 1-continued
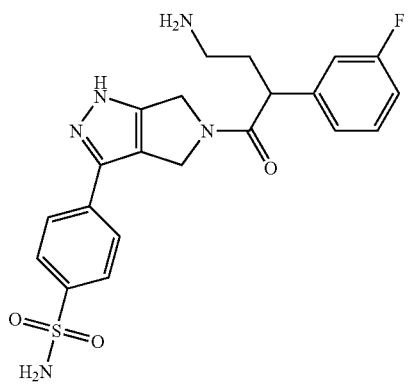
I-175
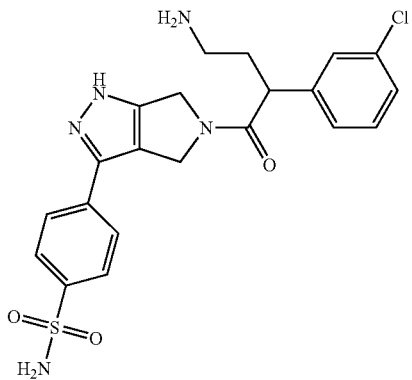
I-174
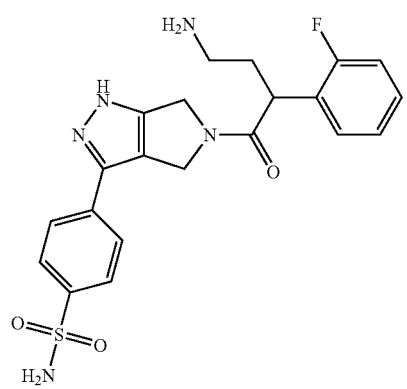
I-176
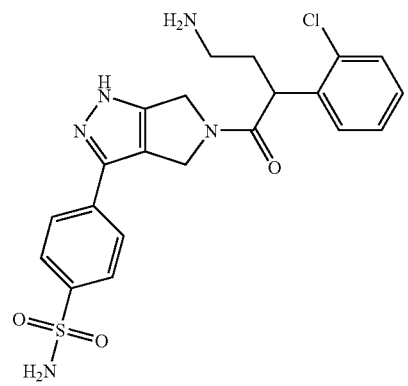
I-179
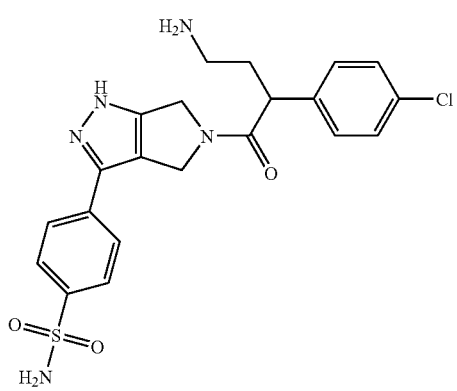
I-177
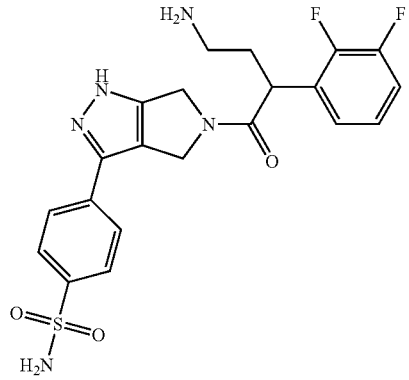
I-180

TABLE 1-continued
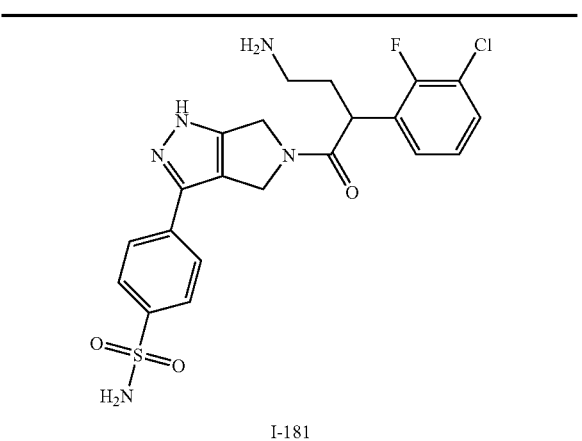
I-181
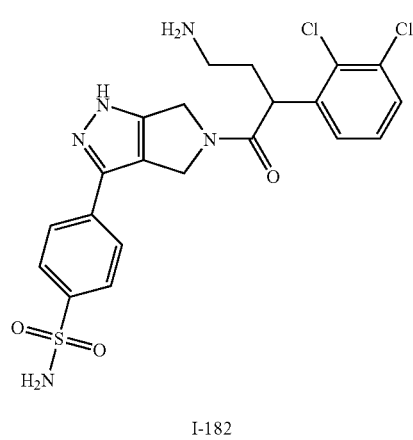 [SMILES: NCCC(C(=O)N1Cc2[nH]nc(-c3ccc(S(N)(=O)=O)cc3)c2C1)c1cccc(Cl)c1Cl ; "I-182"]
I-182
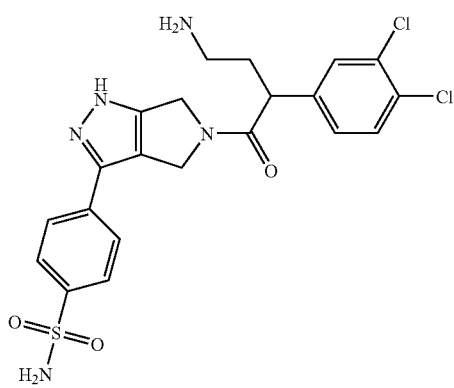
I-183
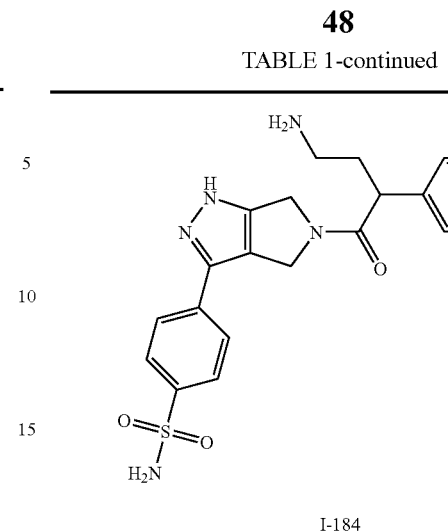
I-184
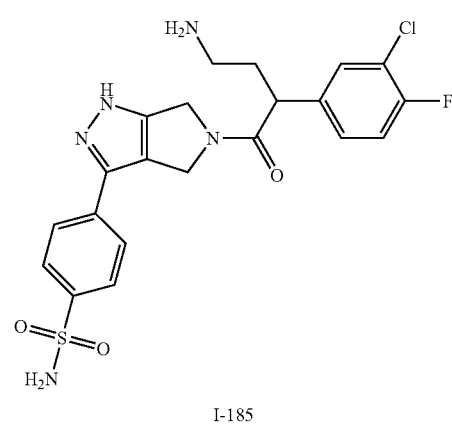 [SMILES: NCCC(C(=O)N1Cc2[nH]nc(-c3ccc(S(N)(=O)=O)cc3)c2C1)c1ccc(F)c(Cl)c1]
I-185
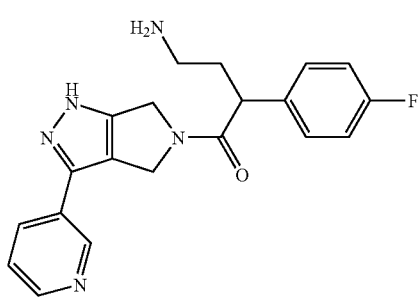
I-186
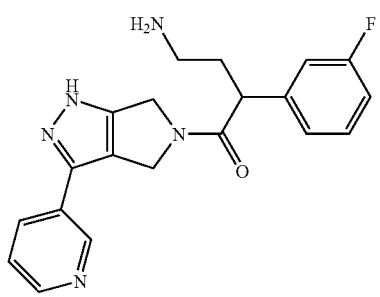
I-187

TABLE 1-continued
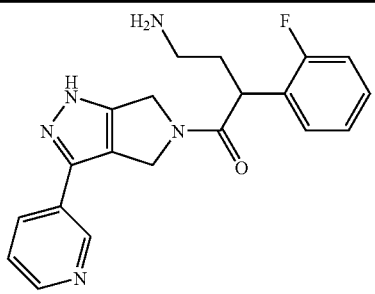
I-188
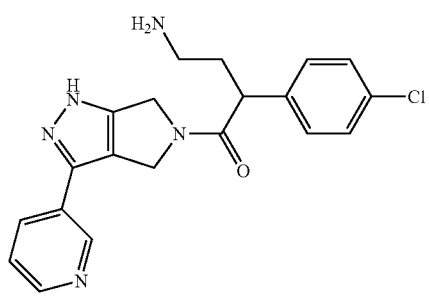
I-189
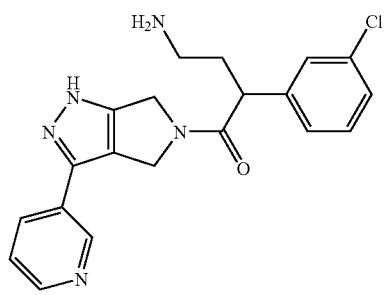
I-190
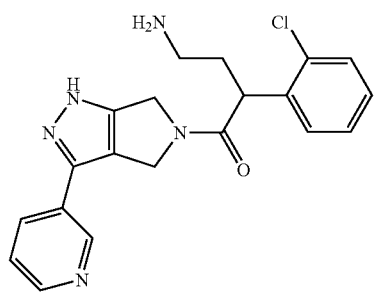
I-191
TABLE 1-continued
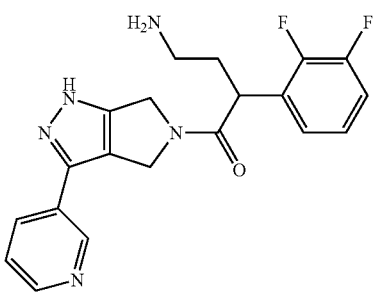
I-192
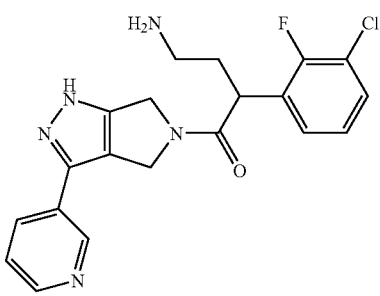
I-193
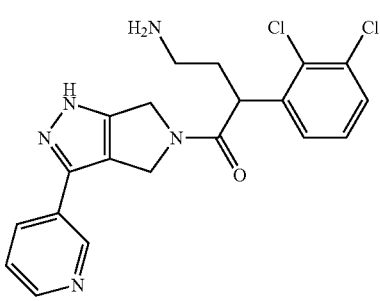
I-194
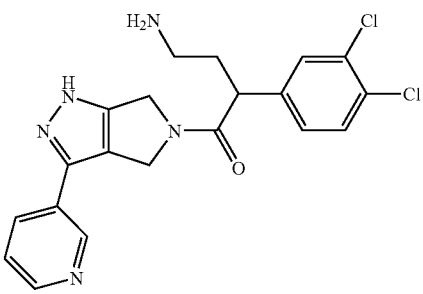
I-195

TABLE 1-continued
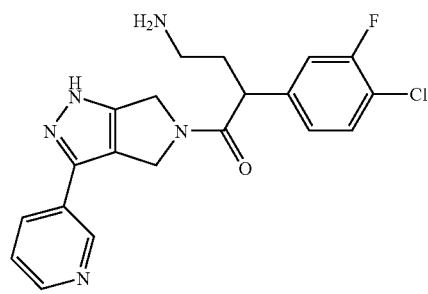
I-196
TABLE 1-continued
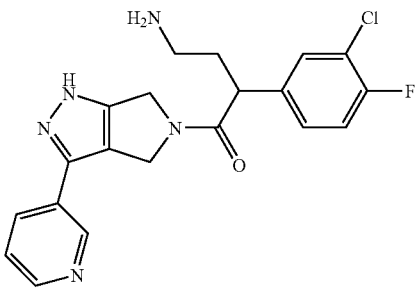
I-197
The compounds of the present invention may be prepared as illustrated by the Schemes I, II, and III below, by the Synthetic Examples described herein, and by general methods known to those of ordinary skill in the art.
Scheme 1
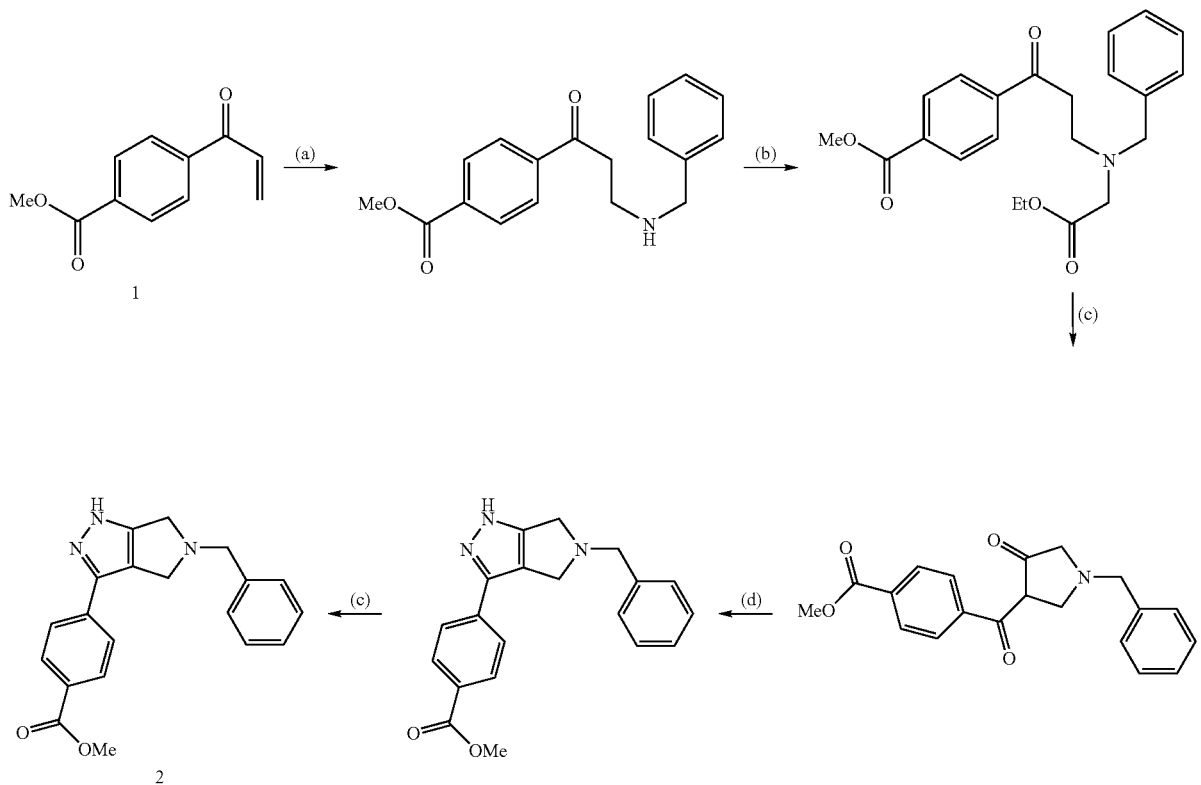
Reagents: (a) benzylamine, THF, 60° C.; (b) BrCH$_2$CO$_2$Et, DMF, 60° C.; (c) NaOEt, toluene; (d) N$_2$H$_4$·H$_2$O, EtOH; (e) LiOH, THF, H$_2$O Scheme I above shows a method for preparing tetrahydro-pyrrolo[3,4-c]pyrazoles. The tetrahydro-pyrrolo[3,4-c]pyrazoles 2 can be prepared in 5 steps from 4-acryloyl-benzoic acid methyl ester 1 by methods substantially similar to that described by Kikuchi, K. et. al., *J. Med. Chem.*, 2000, 43, 409-419.

Scheme III above shows a general method for preparing tetrahydro-pyrrolo[3,4-c]pyrazoles 5.

Accordingly, another embodiment of this invention provides a process for preparing a compound of this invention according to the methods of Schemes I, II, or III.

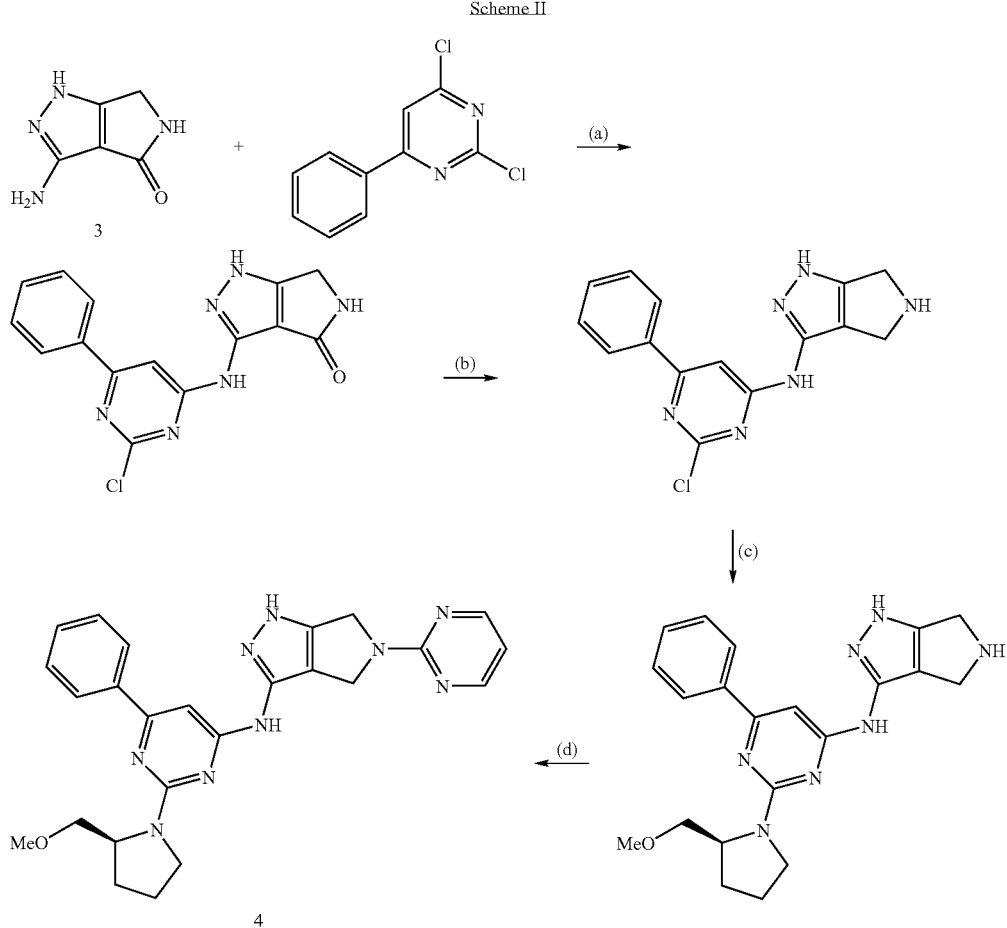

Reagents: (a) 2,4-dichloro-6-phenylpyrimidine, NaI, Et$_3$N, DMF; (b) LiAlH$_4$; (c) (2S)-methoxymethylpyrrolidine, BuOH; (d) 2-chloropyrimidine, BuOH Scheme II above shows an alternative method for preparing tetrahydro-pyrrolo[3,4-c]pyrazoles. The formation of the tetrahydro-pyrrolo[3,4-c]pyrazole 4 is achieved in 4 steps from 3. 3-Amino-5,6-dihydro-1H-pyrrolo[3,4-c]pyrazol-4-one 3 is synthesized in a manner substantially similar to that described by Gelin, S. et al., *Synth. Commun.*, 1982, 12 (6), 431-437.

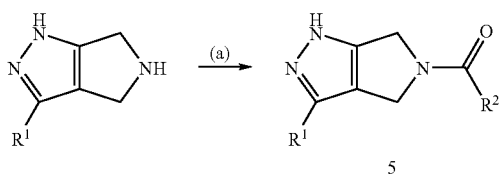

Reagents: (a) R$^2$COOH, EDC, HOBT

The activity of a compound utilized in this invention as an inhibitor of AKT or PDK1 kinase may be assayed in vitro, in vivo or in a cell line according to methods known in the art. In vitro assays include assays that determine inhibition of either the phosphorylation activity or ATPase activity of activated AKT or PDK1. Alternate in vitro assays quantitate the ability of the inhibitor to bind to AKT or PDK1 Inhibitor binding may be measured by radiolabelling the inhibitor prior to binding, isolating the inhibitor/AKT or inhibitor/PDK1 complex and determining the amount of radiolabel bound. Alternatively, inhibitor binding may be determined by running a competition experiment where compounds are incubated with AKT or PDK1 bound to known radioligands. Detailed conditions for assaying a compound utilized in this invention as an inhibitor of AKT or PDK1 kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to measurably inhibit a protein kinase, particularly AKT or PDK1 kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "measurably inhibit", as used herein means a measurable change in AKT or PDK1 activity between a sample comprising said composition and an AKT or PDK1 kinase and an equivalent sample comprising AKT or PDK1 kinase in the absence of said composition.

A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of an AKT or PDK1 family kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Exce-lon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting AKT kinase activity in a biological sample comprising the step of contacting said biological sample with a compound of this invention, or a composition comprising said compound. Preferably, the method comprises the step of contacting said biological sample with a preferred compound of the present invention, as described herein supra.

According to another embodiment, the invention relates to a method of inhibiting PDK1 kinase activity in a biological sample comprising the step of contacting said biological sample with a compound of this invention, or a composition comprising said compound. Preferably, the method comprises the step of contacting said biological sample with a preferred compound of the present invention, as described herein supra.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of AKT or PDK1 kinase activity in a biological sample is useful for a variety of purposes that are known to one of skill in the art. Examples of such purposes include, but are not limited to, blood transfusion, organ-transplantation, biological specimen storage, and biological assays.

Another aspect of this invention relates to a method for treating an AKT-mediated disease in a patient, which method comprises administering to a patient in need thereof, a therapeutically effective amount of a compound of the present invention, or a pharmaceutically acceptable composition comprising said compound. According to a preferred embodiment, the invention relates to administering a preferred compound of formula I, or a pharmaceutically acceptable composition comprising said compound.

Another aspect of this invention relates to a method for treating a PDK1-mediated disease in a patient, which method comprises administering to a patient in need thereof, a therapeutically effective amount of a compound of the present invention, or a pharmaceutically acceptable composition comprising said compound. According to a preferred embodiment, the invention relates to administering a preferred compound of formula I, or a pharmaceutically acceptable composition comprising said compound.

According to another embodiment, the present invention relates to a method for treating an AKT- or PDK1-mediated disease in a patient, which method comprises administering to a patient in need thereof, a therapeutically effective amount of a compound of formula II, III, IV, or V, or a pharmaceutically acceptable composition comprising said compound. According to another embodiment, said method comprises administering to a patient in need thereof, a therapeutically effective amount of a preferred compound of formula II, III, IV, or V, as described herein supra, or a pharmaceutically acceptable composition comprising said compound.

According to another embodiment, the present invention relates to a method for treating an AKT- or PDK1-mediated disease in a patient, which method comprises administering to a patient in need thereof, a therapeutically effective amount of a compound of formula IV or V, or a pharmaceutically acceptable composition comprising said compound. According to another embodiment, said method comprises administering to a patient in need thereof, a therapeutically effective amount of a preferred compound of formula IV, or V, as described herein supra, or a pharmaceutically acceptable composition comprising said compound.

According to another embodiment, the invention provides a method for treating or lessening the severity of an AKT-mediated disease or condition in a patient comprising the step of administering to said patient a composition according to the present invention.

The term "AKT-mediated condition" or "disease", as used herein, means any disease or other deleterious condition in which AKT is known to play a role. The term "AKT-mediated condition" or "disease" also means those diseases or conditions that are alleviated by treatment with an AKT inhibitor. AKT-mediated diseases or conditions include, but are not limited to, proliferative disorders, cancer, cardiovascular disorders, rheumatoid arthritis, and neurodegenerative disorders. Preferably, said cancer is selected from pancreatic, prostate, or ovarian cancer.

According to another embodiment, the invention provides a method for treating or lessening the severity of an PDK1-mediated disease or condition in a patient comprising the step of administering to said patient a composition according to the present invention.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. PDK1-mediated diseases or conditions include, but are not limited to, proliferative disorders, and cancer. Preferably, said cancer is selected from brain (gliomas), breast, colon, head and neck, kidney, lung, liver, melanoma, ovarian, pancreatic, prostate, sarcoma, or thyroid.

According to another embodiment, the present invention relates to a method for treating or lessening the severity of a disease or condition selected from a proliferative disorder, a cardiac disorder, an inflammatory disorder, an autoimmune disorder, a viral disease, or a bone disorder, wherein said method comprises the step of administering an effective amount of a compound of the present invention. Preferably, said method comprises the step of administering an effective amount of a preferred compound of the present invention.

Preferably, the present invention relates to a method for treating or lessening the severity of a cancer.

More preferably, the present invention relates to a method for treating or lessening the severity of a cancer selected from brain (gliomas), breast, colon, head and neck, kidney, lung, liver, melanoma, ovarian, pancreatic, prostate, sarcoma, or thyroid.

Most preferably, the present invention relates to a method for treating or lessening the severity of pancreatic, prostate, or ovarian cancer.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

EXAMPLE 1

AKT-3 Inhibition Assay

Compounds are screened for their ability to inhibit AKT using a standard coupled enzyme assay (Fox et al., Protein Sci., (1998) 7, 2249). Assays are carried out in a mixture of 100 mM HEPES 7.5, 10 mM MgCl2, 25 mM NaCl, 1 mM DTT and 3% DMSO. Final substrate concentrations in the assay are 170 µM ATP (Sigma Chemicals) and 200 µM peptide. Assays are carried out at 30° C. and 45 nM AKT. Final concentrations of the components of the coupled enzyme system are 2.5 mM phosphoenolpyruvate, 300 µM NADH, 30 µg/ML pyruvate kinase and 10 µg/ml lactate dehydrogenase.

An assay stock buffer solution ias prepared containing all of the reagents listed above, with the exception of AKT, DTT, and the test compound of interest. 55 μl of the stock solution is placed in a 96 well plate followed by addition of 2 μl of 1 mM DMSO stock containing the test compound (final compound concentration 30 μM). The plate is pre-incubated for about 10 minutes at 30° C. and the reaction initiated by addition of 10 μl of enzyme (final concentration 45 nM) and 1 mM DTT. Rates of reaction are obtained using a Molecular Devices SpectraMax Plus plate reader over a 15 minute read time at 30° C. Compounds showing greater than 50% inhibition versus standard wells containing the assay mixture and DMSO without test compound are titrated to determine $IC_{50}$ values.

EXAMPLE 2

PDK-1 Inhibition Assay

Compounds are screened for their ability to inhibit PDK-1 using a radioactive-phosphate incorporation assay (Pitt and Lee, J. Biomol. Screen., (1996) 1, 47). Assays are carried out in a mixture of 100 mM HEPES (pH 7.5), 10 mM $MgCl_2$, 25 mM NaCl, 2 mM DTT. Final substrate concentrations in the assay are 40 μM ATP (Sigma Chemicals) and 65 μM peptide (PDKtide, Upstate, Lake Placid, N.Y.). Assays are carried out at 30° C. and 25 nM PDK-1 in the presence of ~27.5 nCi/μL of [γ-$^{32}$P]ATP (Amersham Pharmacia Biotech, Amersham, UK). An assay stock buffer solution is prepared containing all of the reagents listed above, with the exception of ATP, and the test compound of interest. 15 μl of the stock solution is placed in a 96 well plate followed by addition of 1 μl of 0.5 mM DMSO stock containing the test compound (final compound concentration 25 μM, final DMSO concentration 5%). The plate is preincubated for about 10 minutes at 30° C. and the reaction initiated by addition of 4 μl ATP (final concentration 40 μM).

The reaction is stopped after 10 minutes by the addition of 100 μL 100 mM phosphoric acid, 0.01% Tween-20. A phosphocellulose 96 well plate (Millipore, Cat no. MAPH-NOB50) is pretreated with 100 μL 100 mM phosphoric acid, 0.01% Tween-20 prior to the addition of the reaction mixture (100 μL). The spots are left to soak for at least 5 minutes, prior to wash steps (4×200 μL 100 mM phosphoric acid, 0.01% Tween-20). After drying, 20 μL Optiphase 'SuperMix' liquid scintillation cocktail (Perkin Elmer) is added to the well prior to scintillation counting (1450 Microbeta Liquid Scintillation Counter, Wallac).

Compounds showing greater than 50% inhibition versus standard wells containing the assay mixture and DMSO without test compound are titrated to determine $IC_{50}$ values.

The entire disclosure of all documents cited herein are incorporated herein by reference.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound selected from the group consisting of:

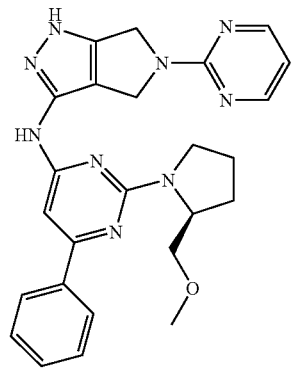

I-28

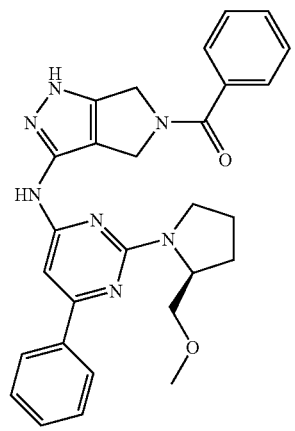

I-29

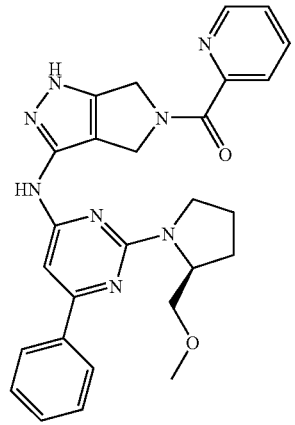

I-30

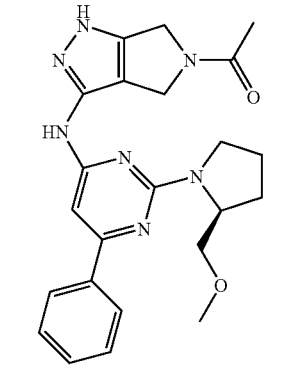

I-31

-continued

I-32
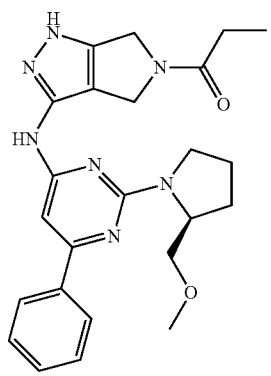

I-33
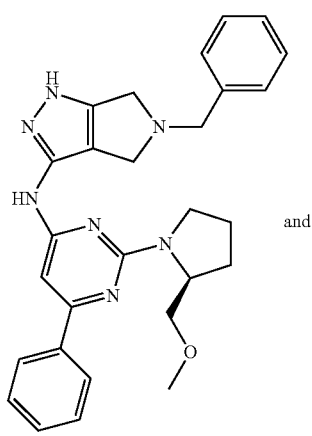
and

I-34
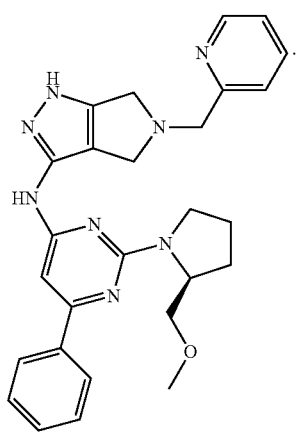

2. A compound selected from the group consisting of:

I-36
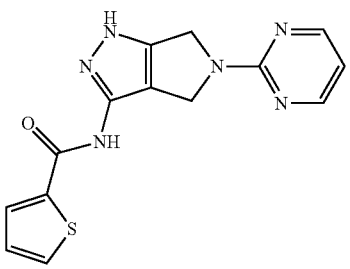

I-37
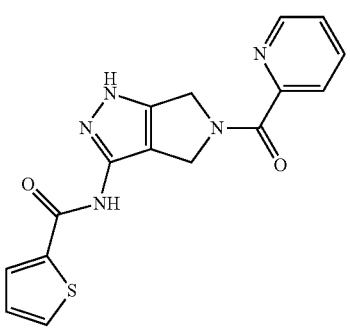

I-42
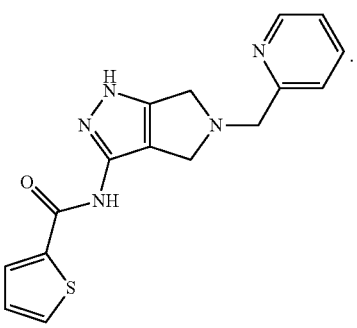

3. A composition comprising a compound according to claim 1 or 2, and a pharmaceutically acceptable carrier, adjuvant, or vehicle.

4. The composition according to claim 3, additionally comprising a therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

* * * * *